US005852168A

United States Patent [19]
Barany et al.

[11] Patent Number: 5,852,168
[45] Date of Patent: Dec. 22, 1998

[54] SULFURIZATION OF PHOSPHORUS-CONTAINING COMPOUNDS

[75] Inventors: George Barany, Falcon Heights, Minn.; Robert P. Hammer, Baton Rouge, La.; Karin Musier-Forsyth, Roseville, Minn.; Qinghong Xu, Lauderdale, Minn.; Lin Chen, Minneapolis, Minn.

[73] Assignees: Regents of the University of Minesota, Minneapolis, Minn.; The Board of Supervisors of LA State University, Baton Rouge, La.

[21] Appl. No.: 641,920

[22] Filed: Apr. 30, 1996

[51] Int. Cl.$^6$ ................................. C07F 9/02; C07F 1/00; C07F 1/107

[52] U.S. Cl. .......................... 530/345; 530/330; 530/331; 530/404; 536/25.3; 536/25.34; 548/129; 548/130; 558/122; 558/124

[58] Field of Search ...................................... 558/122, 124, 558/129; 530/330, 331, 345, 404; 536/25.3, 25.34; 548/130, 129

[56] References Cited

U.S. PATENT DOCUMENTS

| | | | |
|---|---|---|---|
| 4,415,732 | 11/1983 | Caruthers et al. | 536/27 |
| 5,003,097 | 3/1991 | Beaucage et al. | 558/129 |
| 5,395,928 | 3/1995 | Bergot | 536/25.4 |

FOREIGN PATENT DOCUMENTS

| | | |
|---|---|---|
| 682820 | 12/1966 | Belgium . |
| 1224720 | 9/1966 | Germany . |
| 8902521 | 5/1997 | Netherlands . |
| 1136737 | 12/1968 | United Kingdom . |
| WO91/16331 | 10/1991 | WIPO . |
| WO92/14742 | 3/1992 | WIPO . |

OTHER PUBLICATIONS

Xu, Q. et al., "Use of 1,2,4–dithiazolidine–3,5–dione (DtsNH) and 3–ethoxy–1,2,4–dithiazoline–5–one (EDITH) for synthesis of phosphorothioate–containing oligodeoxyribonucleotides," *Nucleic Acids Research*, 24(9), 1602–1607 (1996).

Xu, Q. et al., "Efficient introduction of phosphorothioates into RNA oligonucleotides by 3–ethoxy–1,2, 4–dithiazoline–5–one (EDITH)," *Nucleic Acids Research*, 24(18), 3643–3644 (1996).

Xu, Q. et al., "N–Dithiasuccinoyl (DTS)–Amines: Novel Sulfurizing Reagents for the Solid–Phase Preparation of Thiophosphopeptides and Oligodeoxyribonucleoside Phosphorothioates," *Innovation and Perspectives in Solid Phase Synthesis & Combinatorial Libraries*, Ed., R. Epton Fourth International Symposium, Sep. 12–16, 1995, Edinburgh, Scotland, U.K. (1996).

N.I.H. Grant No. 28934 Abstract (1986).
N.I.H. Grant No. 42722 Abstract (1992).
N.I.H. Grant No. 43552 Abstract (1989).
N.I.H. Grant No. 49928 Abstract (1992).
N.S.F. Grant No. CHE–9500992 (1995).

Agrawal et al., "Efficient Synthesis of Oligoribonucleotide and its Phosporothioate Analogue Using H–Phosphonate Approach," *Tetrahedron Lett.*, 31(52) 7541–7544 (1990).

Ausserer et al., "High–Resolution Analysis and Purification of Synthetic Oligonucleotides with Strong Anion–Exchange HPLC," *Biotechniques*, 19(1) 136–139 (1995).

Barany et al., "A General Strategy for Elaboration of the Dithiocarbonyl Functionality –(C=0)SS–: Application to the Synthesis of Bis(chlorocarbonyl)disculfane and Related Derivatives of Thiocarbonic Acids," *J. Org. Chem.*, 48(24) 4750–4761 (1983).

Barelli et al., "Potent inhibition of endopeptidase 24.16 and endopeptidase 24.15 by the phosphonamide peptide N–(phenylethylphosphonyl)–Gly–L–Pro–Laminohexanoicacid," *Biochem. J.*, 287 (Part 2) 621–625 (1992).

Bongartz et al., "Improved Biological activity of antisense oligonucleotides conjugated to a fusogenic peptide," *Nucleic Acids Research*, 22(22) 4681–4688 (1994).

Cao et al., "Layered Metal Phosphates and Phosphonates: From Crystals to Monolayers," *Acc. Chem. Res.*, 25(9) 420–427 (1992).

Connolly et al., "Synthesis and Characterization of an Octanucleotide Containing the EcoRI Recognition Sequence with a Phosphorothioate Group at the Cleavage Site," *Biochemistry*, 23:3443–3453 (1984).

de Bont et al., "Solid–Phase Synthesis of o–Phosphorothioylserine– and –threonine–Containing Peptides as Well as of o–Phosphoserine– and –threonine–Containing Peptides," *J. Org. Chem.*, 58 1309–1317 (1993).

Eckstein et al., "Phosphorothioates in molecular biology," *TIBS*, 14 97–100 (1989).

Efimov et al., "New efficient sulfurizing reagents for the preparation of oligodeoxyribonucleotide phosphorothioate analogues," *Nucleic Acids Research*, 23(20) 4029–4033 (1995).

Fernandez et al., "Synthesis of Phosphonate and Thiophosphonate Esters and Amides from Hydrogen–Phosphinates by a Novel One–Pot Activation–Coupling Oxidation Procedure," *J.Org. Chem.*, 60 7390–7391 (1995).

Fidanza et al., "Site–Specific Labeling of DNA Sequences Containing Phosphorothioate Diesters," *J. Am. Chem. Soc.*, 114 5509–5517 (1992).

Froehler, "Deoxynucleoside H–Phosphonate Diester Intermediates in the Synthesis of Internucleotide Phosphate Analogues," *Tetrahedron Lett.*, 27(46) 5575–5578 (1986).

Garegg et al., "Formation of Internucleotidic Bonds via Phosphonate Intermediates," *Chemica Scripta*, 25 280–282 (1985).

Harris, "The Reactions of Sulfenyl chlorides with Thionocarbamates," *Sulfenyl Chlorides with Thionocarbomates* 82 155–158 (1960).

(List continued on next page.)

Primary Examiner—Richard L. Raymond
Attorney, Agent, or Firm—Mueting Raasch Gebhardt

[57] ABSTRACT

The present invention provides a method for sulfurizing a phosphorus-containing compound, such as a trivalent phosphorus compound, using a disulfide-containing five-membered heterocycle.

27 Claims, 13 Drawing Sheets

OTHER PUBLICATIONS

Iyer et al., "The Automated Synthesis of Sulfur–Containing Oligodeoxyribonucleotides Using 3H–1,2–Benzodithiol–3–one 1,1–Dioxide as a Sulfur–Transfer Reagent," *J. Org. Chem.*, 55 4693–4699 (1990).

Kaplan et al., "Synthesis and Evaluation of an Inhibitor of Caroxypeptidase A with a $K_i$ Value in the Femtomolar Range," *Biochemistry*, 30(33) 8165–8170 (1991).

Kitas et al., "Chemical synthesis of o–thiophosphotyrosyl peptides," *Int. J. Peptide Protein*, 43 146–153 (1994).

Koziolkiewicz et al., "Application of Phosphate–Backbone–Modified Oligonucleotides in the Studies on EcoRI Endonuclease Mechanism of Action," *Biochemistry*, 31 9460–9466 (1992).

Maiti et al., "Phosphorus–Containing Polymers," *Prog. Polym. Sci.*, 18(2) 227–261 (1993).

Martin et al., "General Method for the Synthesis of Phospholipid Derivatives of 1,2–O–Diacyl–sn–glycerols," *J. Org. Chem.*, 59(17) 4805–4820 (1994).

Martin et al., "Design, Synthesis, and Evaluation of Phospholipid Analogues as Inhibitors of the Bacertial Phospholipase C from *Bacilus cereus*," *J. Org. Chem.*, 59(17) 4821–4831 (1994).

Martin et al., "General and Efficient Route to Phosphorodithioate Analogues of Naturally Occurring Lipids," *J. Org. Chem.*, 58(22) 5897–5899 (1993).

Milligan et al., "Determination of RNA–Protein Contacts Using Thiophosphate Substitutions," *Biochemistry*, 28 2849–2855 (1989).

Moore et al., "Evidence for two active sites in the spliceosome provided by sterochemistry of pre–mRNA splicing," *Nature*, 365(1993).

Morgan et al., "Differential Binding Energy: A Detailed Evaluation of the Influence of the Hydrogen–Bonding and Hydrophobic Groups on the Inhibition of Thermolysin by Phosphorus–Containing Inhibitors," *J. Am. Chem. Soc.*, 113(1) 297–307 (1991).

Musier–Forsyth et al., "Acceptor Helix Interactions in a Class II tRNA Synthetase: Photoaffinity Cross–Linking of an RNA Miniduplex Substrate," *Biochemistry*, 33 773–779 (1994).

Ottinger et al., "Synthesis of Phosphotyrosine–Containing Peptides and Their Use as Substrates for Protein Tyrosine Phosphates," *Biochemistry*, 32(16) 4354–4361 (1993).

Rao et al., "Dibenzoyl Tetrasulphide—Rapid Sulphur Transfer Agent in the Synthesis of Phosphorothioate Analogues of Oligonucleotides," *Tetrahedron Lett.*, 33(33) 4839–4842 (1992).

Rao et al., "Solid Phase Synthesis of Phosphorothioate Oligonucleotides Using Benzyltriethylammonium Tetrathiomolybdate as a Rapid Sulfur Transfer Reagent," *Tetrahedron Lett.*, 35(36) 6741–6744 (1994).

Roelen et al., "A study on the use of phenylacetyl disulfide in the solid–phase synthesis of oligodeoxynucleoside phosphorothioates," *Recl. Trav. Chim. Pays–Bas*, 110 325–331 (1991).

Slomczynska et al., "Efficient Synthesis of 1,2,4–Dithiazolidine–3,5–diones (Dithiasuccinoyl–amines) and Observations on Formation of 1,2,4–Thiadiazolidine–3,5–diones by Related Chemistry," *J. Heterocyclic Chem.*, 21 241–246 (1984).

Sproat et al., "An Efficient Method for the Isolation and Purification of Oligoribonucleotides," *Nucleosides and Nucleotides*, 14(1&2) 255–273 (1995).

Stec et al., "Stereocontrolled Synthesis of Oligo(nucleoside phosphorothioate)s," *Agnew. Chem. Int. Ed. Engl.*, 33(7) 709–722 (1994).

Stec et al., "Automated Solid–Phase Synthesis, Separation, and Sterochemistry of Phosphorothioate Analogues of Oligodeoxyribonucleotides," *J. Am. Chem.*, 106 6077–6079 (1984).

Stec et al., "Bis(O,O–Diisopropoxy Phosphinothioyl) Disulfide—A Highly Efficient Sulfurizing Reagent for Cost–Effective Synthesis of Oligo(Nucleoside Phosphorothioate)s" *Tetrahedron Lett.*, 34(33) 5317–5320 (1993).

Tegge, "Solid–phase syntheses of phosphorylated and thiophosphorylated peptides related to an EGFR sequence," *Int. J. Peptide Protein Res.*, 43 448–453 (1994).

Uhlman et al., "Antisense Oligonucleotides: A New Therapeutic Principle," *Chemical Reviews*, 90(4) 544–584 (1990).

Vu et al., "Internucleotide Phosphite Sulfurization with Tetraethylthiuram Disulfide Phosphorothioate Oligonucleotide Synthesis Via Phosphoramidite Oligonucleotide Synthesis Via Phosphoramidite Chemistry" *Tetrahedron Lett.*, 32(26) 3005–3008 (1991).

Vyle et al., "New Methods for Synthesis of 3'–S–Phosphorothiolate Internucleoside Linkages," *Tetrahedron Lett.*, 33(21) 3017–3020 (1992).

Wagner, "Gene inhibition using antisense oligodeoxynucleotides," *Nature*, 372 333–335 (1994).

Wheeler et al., "On the Rearrangement of the Thioncarbamic Esters," *Am. Chem., J.*, 22 141–151 (1899).

Xu et al., "N–Dithiasuccinoyl (DTS)–Amines: Novel Sulfurizing Reagents for the Solid–Phase Preparation of Thiophosphopeptides and Oligodeoxyribonucleoside Phosphorothioates," Abstract and Poster Presentation, 10 pp. (Jun. 1995).

Zon et al., "Phosphorothioate oligonucleotdies: chemistry, purification, analysis, scale–up and future directions," *Anti–Cancer Drug Design*, 6 539–568 (1991).

Zumach et al., "Chlorosulfenylated Carbonic Acid Derivatives," *Agnew. Chem. Interat. Edit.*, 9(1) 54–63 (1970).

Zon et al., "Phosphorothioate oligonucleotides," *Oligonucleotides and Analogues*, Chapter 4, 87–108 (1991).

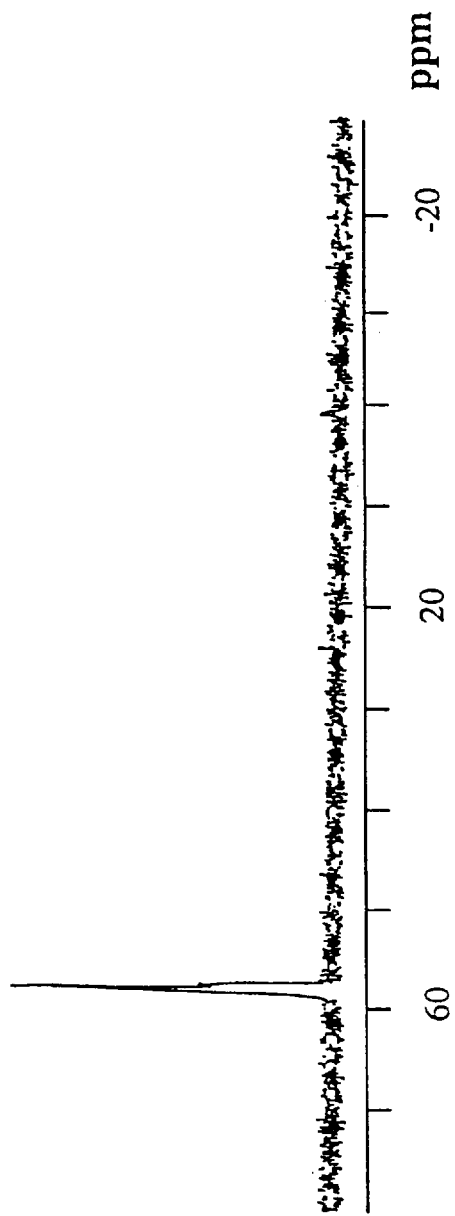

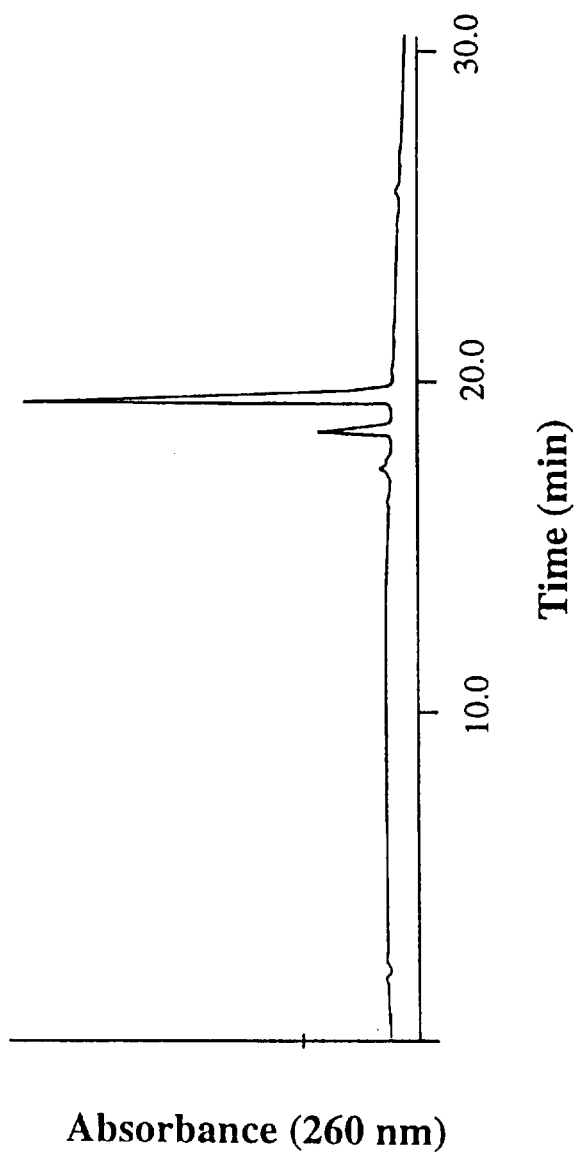

SULFURIZATION OF PHOSPHORUS-CONTAINING COMPOUNDS

STATEMENT OF GOVERNMENT RIGHTS

This invention was made with government support under Grant Nos. GM 28934, GM 42722, GM 43552, and GM 49928, awarded by the National Institutes of Health and Grant No. CHE-95000992, awarded by the National Science Foundation. The government has certain rights in the present invention.

BACKGROUND OF THE INVENTION

Phosphorothioate analogues of the phosphate moiety in compounds are of considerable interest in nucleic acid research, protein research, etc. For example, phosphorothioate-containing antisense oligonucleotides have been used in vitro and in vivo as inhibitors of gene expression. Site-specific attachment of reporter groups onto the DNA or RNA backbone is facilitated by the incorporation of single phosphorothioate moieties. Phosphorothioates have also been introduced into oligonucleotides for mechanistic studies on DNA-protein and RNA-protein interactions, as well as catalytic RNAs.

Introduction of phosphorothioate moieties into oligonucleotides, assembled by solid-phase synthesis, can be achieved readily using either an H-phosphonate approach or a phosphoramidite approach. The H-phosphonate approach involves a single sulfur transfer step, carried out after the desired sequence has been assembled, to convert all of the internucleotide linkages to phosphorothioates. Alternatively, the phosphoramidite approach features a choice at each synthetic cycle: a standard oxidation provides the normal phosphodiester internucleotide linkage, whereas a sulfurization step introduces a phosphorothioate at that specific position in the sequence. An advantage of using phosphoramidite chemistry, therefore, is the capability to control the state of each linkage [$P=O$ vs. $P=S$] in a site-specific manner. The earliest studies to create phosphorothioates used elemental sulfur, but the success of the phosphoramidite approach is dependent on the availability and application of more efficient, more soluble sulfur transfer reagents that are compatible with automated DNA synthesis.

With these goals in mind, a number of reagents have been designed and tested in recent years. These include 3H-1,2-benzodithiol-3-one-1,1-dioxide ("Beaucage reagent") which is disclosed in Iyer et al., *J. Org. Chem.*, 55, 4693–4699 (1990) and U.S. Pat. No. 5,003,097 (Beaucage et al.), tetraethylthiuram disulfide ("TETD"), which is disclosed in Vu et al., *Tetrahedron Lett.*, 32, 3005–3008 (1991), phenylacetyl disulfide, which is disclosed in Roelen et al, *Recl. Trav. Chim. Pays-Bas.*, 110, 325–331 (1991), dibenzoyl tetrasulfide, which is disclosed in Rao et al., *Tetrahedron Lett.*, 33, 4839–4842 (1992), bis(O,O-diisopropoxy phosphinothioyl) disulfide ("S-Tetra"), which is disclosed in Stec et al., *Tetrahedron Lett.*, 34, 5317–5320 (1993), benzyltriethylammonium tetrathiomolybdate ("BTTM"), which is disclosed in Rao et al., *Tetrahedron Lett.*, 35, 6741–6744 (1994), and bis(4-methoxybenzenesulfonyl) disulfide and related aryl derivatives, as disclosed in Efimov et al., *Nucleic Acids Res.*, 23, 4029–4033 (1995). Of the listed compounds, the Beaucage reagent has been used widely due to its commercial availability and favorable kinetics and effectiveness. However, the synthetic accessibility, solubility properties, and stability of the Beaucage reagent are not optimal, and its suitability for large-scale oligonucleotide preparation has been questioned. Thus, what is needed are alternative sulfurizing reagents and methods for sulfur transfer that are compatible with standard automated DNA and RNA synthesis.

Phosphorus derivatives of peptides are becoming increasingly important in chemical and biological research. Phosphorylated proteins, whereby a phosphate monoester is formed with the side-chain hydroxyl group of serine, threonine, or tyrosine, have been identified as key intermediates in protein regulation and signal transduction by protein kinases and phosphatases. Recently, phosphorylated peptides (phosphopeptides) have been made available by advances in synthetic methodology (Ottinger, et al., *Biochemistry*, 32, 4354–4361 (1993); de Bont et al., *J. Org. Chem.*, 58, 1309–1317 (1993); and Kitas et al., *Int. J. Peptide Protein Res*, 43, 146–153 (1994)); and are being employed to understand the mechanism of action of phosphorylation and the role of phosphorylation in the disease. Thiophospho-, dithiophospho-, thiophosphono-, and dithiophosphono-analogues of phosphorylated peptides as envisioned in this invention will be key to advancements in these fields.

Another important class of phosphorus-containing peptides are derivatives in which the carboxamide linkage between two amino acids is replaced by a phosphono group (i.e., $P=O$ group). These peptide-mimics or pseudopeptides, referred to as phosphonopeptides, have been found to be effective inhibitors of three major classes of proteolytic enzymes—serine, aspartyl and zinc proteases (Kaplan et al., *Biochemistry*, 30, 8165–8170 (1991); Morgan et al., *J. Am. Chem. Soc.*, 113, 297–307 (1991); and Barelli et al., *Biochem. J.*, 287, 621–625 (1992))—by acting as transition state analogues of the natural enzyme substrates. Thiophosphonopeptides have been prepared for the first time recently by Fernandez, *J. Org. Chem.*, 60, 7390–7391 (1995) using trivalent phosphonoamino acids as intermediates and then sulfurizing them. These will be of potential use as new protease inhibitors.

Other phosphorus-containing materials of interest include phospholipids, phosphorus-containing polymers, and phosphonate modified surfaces. Thioderivatives of the phospholipids, which have interesting bioactivities, have been prepared by Martin et al., *J. Org. Chem.*, 58, 5897–5899 (1993); Martin et al., *J. Org. Chem.*, 59, 4805–4820 (1994); and Martin et al., *J. Org. Chem.* 59, 4821–4831 (1994). Certain phosphorus polymers containing the thiophospho function (i.e., $S=P(R)_3$, where R is an alkyl group or heteroatom-containing alkyl group) are disclosed by Maiti et al., *Progress in Polymer Science*, 18, 227–261 (1993) and are useful as flame retardants. Surfaces modified with phosphonates have allowed for the preparation of metal-organic multilayers, similar to Langmuir-Blodget films. Such metal organic multilayers have many applications including chemo-selective and type-selective crystal growth and as chemoselective sensors (Cao et al., *Accounts of Chemical Research*, 25, 420–427 (1992). Thus, what is needed are additional sulfurizing reagents that provide access to this wide variety of materials.

SUMMARY OF THE INVENTION

The present invention provides a method of sulfurizing phosphorus-containing compounds. The method involves contacting the compound to be sulfurized with a compound of the formula (Formula I):

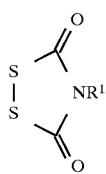

or a compound of the formula (Formula II):

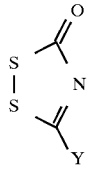

wherein: $Y=R^2$, $R^3$, $NR^{16}R^{17}$, or $SR^{18}$; each $R^1$, $R^{16}$, and $R^{17}$ is independently H or an organic group; and each $R^2$, $R^3$, and $R^{18}$ is independently an organic group. Preferably, each $R^1$, $R^2$, $R^3$, $R^{16}$, $R^{17}$, and $R^{18}$ is independently an organic group (preferably an alkyl or an aryl group) having 1–20 carbon atoms. Particularly preferred compounds are those wherein $R^1=H$ for Formula I and $Y=OR^3$ wherein $R^3$ is an ethyl group for Formula II.

The phosphorus-containing compound is preferably a trivalent phosphorus compound of the formula (Formula III):

wherein X, W, and Z are organic groups. Preferably, X and Z are independently selected from the group consisting of —$R^4$, —O—$R^5$, —C($R^6$)($R^7$)($R^8$), —NH($R^9$), —N($R^{10}$)($R^{11}$) or —S—$R^{12}$; W is selected from the group consisting of —$R^4$, —O—$R^5$, —C($R^6$)($R^7$)($R^8$), —NH($R^9$), —N($R^{10}$)($R^{11}$) or —S—$R^{12}$, halogen, or a protecting group; and each R group is independently selected from the group consisting of aryl groups, alkyl groups, alicyclic groups, carbohydrate groups, glyceride groups, peptide groups, nucleoside groups, amino acid groups, steroidal groups, terpene groups, oligonucleotide groups, phosphonopeptide groups, phospholipid groups, phosphorus-containing polymeric groups, and phosphonate-modified surfaces.

The present invention also provides a method of preparing a compound of the formula (Formula II):

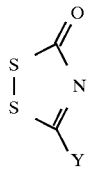

wherein: $Y=R^2$, $OR^3$, $NR^{16}R^{17}$, or $SR^{18}$; each $R^1$, $R^{16}$, and $R^{17}$ is independently H or an organic group having 1–20 carbon atoms; and each $R^2$, $R^3$, and $R^{18}$ is independently an organic group having 1–carbon atoms; the method comprising combining a thioamide (thiourea, or dithiocarbamate, a thiocarbamate, dithiocarbamate, or thiourea) with (chlorocarbonyl)sulfenyl chloride in a nonhalogenated solvent.

DETAILED DESCRIPTION

Figure 1:
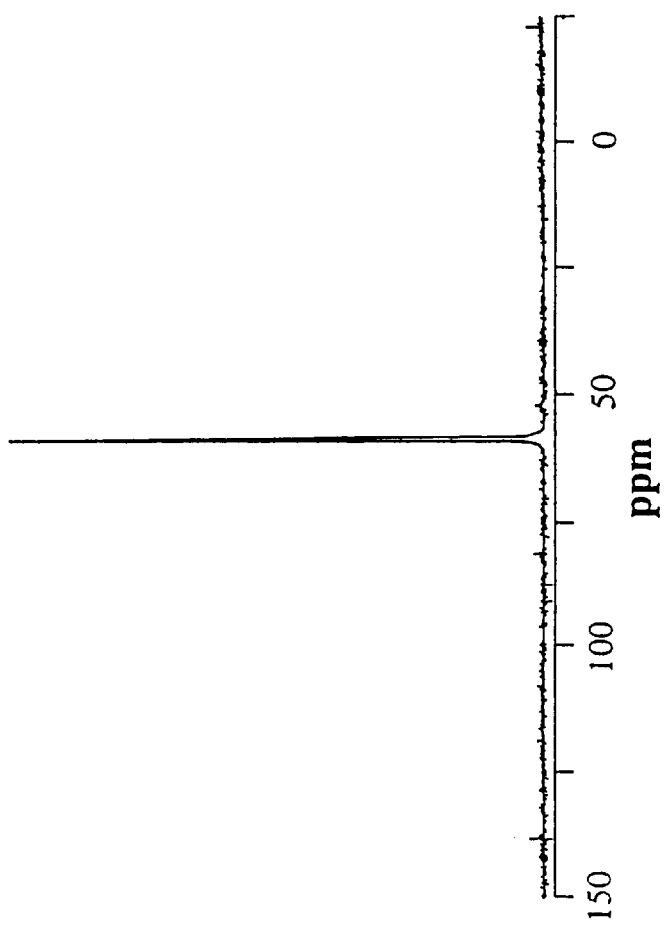
FIG. 1. $^{31}$P NMR [single peak at δ57 ppm] of the oligodeoxyribonucleotide S-d($T_{19}$A) synthesized on a 1.0 μmol scale, with multiple phosphorothioate linkages established by 30 second reactions with 0.05M 3-ethoxy-1,2,4,-dithiazoline-5-one (EDITH) in $CH_3CN$.

The present invention provides a method for sulfurizing a phosphorus-containing compound, such as a trivalent phosphorus compound, particularly a method for the preparation of phosphorothioate-containing compounds. Specifically, the present invention provides a method for the incorporation of phosphorothioate linkages (P=S) into a variety of biologically important molecules, such as DNA, RNA, and phosphopeptides, for example.

The method of the present invention involves the use of a compound of the formula (Formula I):

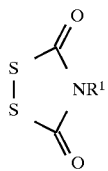

or a compound of the formula (Formula II):

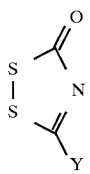

wherein Y=$R^2$, $OR^3$, $NR^{16}R^{17}$, or $SR^{18}$; each $R^1$, $R^{16}$, and $R^{17}$ is independently H or an organic group, preferably containing 1–carbon atoms, and more preferably containing 1–10 carbon atoms, that does not interfere with the sulfurization reaction; and each $R^2$, $R^3$, and $R^{18}$ is independently an organic group, preferably containing 1–20 carbon atoms, and more preferably containing 1–10 carbon atoms, that does not interfere with the sulfurization reaction. The compound of Formula I, includes, for example:

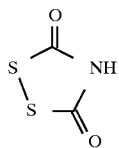

which is 1,2,4-dithiazolidine-3,5-dione ("DtsNH"), and a variety of N-substituted dithiazolidine-3,5-dione compounds. The compound of Formula II includes, for example:

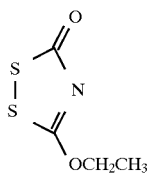

which is 3-ethoxy-1,2,4-dithiazoline-5-one ("EDITH"), and a variety of other 3-alkyl, 3-aryl, 3-alkoxy-, and 3-aryloxy-1,2,4-dithiazoline-5-ones, for example. The compounds of Formula I and II are referred to herein as sulfur-transfer reagents or sulfurizing reagents.

As used herein, the term "organic group" means a hydrocarbon group that is classified as an aliphatic group, cyclic group, or combination of aliphatic and cyclic groups (e.g., alkaryl and aralkyl groups). In the context of the present invention, the term "aliphatic group" means a saturated or unsaturated linear or branched hydrocarbon group. This term is used to encompass alkyl, alkenyl, and alkynyl groups, for example. The term "alkyl group" means a saturated linear or branched hydrocarbon group including, for example, methyl, ethyl, isopropyl, t-butyl, heptyl, dodecyl, octadecyl, amyl, 2-ethylhexyl, and the like. The term "alkenyl group" means an unsaturated, linear or branched hydrocarbon group with one or more carbon-carbon double bonds, such as a vinyl group. The term "alkynyl group" means an unsaturated, linear or branched hydrocarbon group with one or more carbon—carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or aryl group" means a mono- or polynuclear aromatic hydrocarbon group. The term "heterocyclic group" means a closed ring hydrocarbon in which one or more of the atoms in the ring is an element other than carbon (e.g., a heteroatom, such as nitrogen, oxygen, sulfur, etc.).

As is well understood in this technical area, a large degree of substitution is not only tolerated, but is often advisable. Substitution is anticipated on the compounds of the present invention. As a means of simplifying the discussion and recitation of certain terminology used throughout this application, the terms "group" and "moiety" are used to differentiate between chemical species that allow for substitution or that may be substituted and those that do not allow or may not be so substituted. Thus, when the term "group" is used to describe a chemical substituent, the described chemical material includes the unsubstituted group and that group with O, N, or S atoms, for example, in the chain as well as carbonyl groups or other conventional substitution. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, t-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, t-butyl, and the like.

Preferably, each $R^1$, $R^2$, $R^3$, $R^{16}$, $R^{17}$, and $R^{18}$ is independently an alkyl group or an aryl group. More preferably, the R groups of Formulas I and II are each independently a ($C_1$–$C_{10}$)alkyl or ($C_1$–$C_{10}$)aryl group, and most preferably a ($C_1$–$C_4$)alkyl group. Typically, these alkyl groups are unsubstituted (i.e., they are preferably alkyl moieties). Thus, two particularly preferred compounds of Formula II are 3-ethoxy-1,2,4-dithiazoline-5-one ("EDITH"), wherein Y=$OR^3$ and $R^3$=ethyl, and 3-methyl-1,2,4-dithiazoline-5-one, wherein Y=$R^2$ and $R^2$=methyl.

DtsNH is the simplest member (i.e., no substituent on nitrogen) of a family of disulfide-containing five-membered heterocycles that have been adapted for amino group protection. Dts is an acronym for "dithiasuccinoyl," which emphasizes how the heterocycle is viewed as an amine masked with two molecules of carbonyl sulfide (COS). The parent amine is released when the heterocyclic disulfide is reduced by a variety of agents including thiols and borohydrides. Dts-amines can also be viewed as masked isocyanates, a dissection that gives rise to one molecule of COS as well as monomeric "sulfur."

The method of the present invention typically involves contacting a compound of Formula I or II with a phosphorus-containing compound, in a solvent or mixture of solvents. The phosphorus in the phosphorus-containing compound is typically a trivalent phosphorus (i.e., P(III) with one lone pair and three single bonds). Upon sulfurization, it becomes a pentavalent phosphorus (i.e., P(V) with one double bond to a sulfur atom and three single bonds). The trivalent phosphorus can be a phosphite, phosphonite, phophonamidite, phosphoramidite, phosphine or any other phosphorus (III) derivative as part of the synthesis of DNA, RNA, phosphoropeptides, phosphonopeptides, phosphorylated nucleoside sugars, or oligosaccharides or any other thiolated phosphorus (V) derivatives prepared either in solution or in the solid-phase.

Preferably, the phosphorus-containing compound of the formula (Formula III):

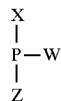

is converted to a compound of the formula (Formula IV):

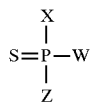

using the method of the present invention. In Formula III and Formula IV, the substituents X, W, and Z are organic groups, as defined above, which may or may not be polymeric groups. Preferably, X and Z are independently selected from the group consisting of $-R^4$, $-O-R^5$, $-C(R^6)(R^7)(R^8)$, $-NH(R^9)$, $-N(R^{10})(R^{11})$ or $-S-R^{12}$; W is selected from the group consisting of $-R^4$, $-O-R^5$, $-C(R^6)(R^7)(R^8)$, $-NH(R^9)$, $-N(R^{10})(R^{11})$ or $-S-R^{12}$, halogen, or a protecting group. Each X, W, and Z may be the same or different. Also, each R group (i.e., $R^4-R^{12}$) may be the same or different, and are preferably selected from the group consisting of aryl groups, alkyl groups, alicyclic groups, carbohydrate groups, glyceride groups, peptide groups, nucleoside groups, amino acid groups, steroidal groups, terpene groups, oligonucleotide groups, phosphonopeptide groups, phospholipid groups, phosphorus-containing polymeric groups, and phosphonate-modified surfaces. Preferably, the R groups are alkyl groups (preferably ($C_1-C_8$)alkyl groups), peptide groups, and oligonucleotide groups. More preferably, the R groups of Formula III are peptide and oligonucleotide groups.

Referring to Formula III, the term "carbohydrate groups" means polyhydroxy aldehyde groups, polyhydroxy ketone groups and other groups that can be hydrolyzed to the same. Monosaccharidic, disaccharidic, and polysaccharidic groups that may or may not carry specific hydroxy protecting groups, are included within the scope of this term. The term "glyceride group" means glycerol groups that may or may not carry specific hydroxy protecting groups. The term "peptide group" means amide-containing groups formed by the interaction between amino groups and carboxyl groups of amino acids. This term encompasses dipeptides, tripeptides, and polypeptides up to a molecular weight of 10,000, that may or may not carry specific hydroxy protecting groups. The term "nucleoside group" is one that is formed from a sugar (notably ribose or deoxyribose) with a purine or pyrimidine base by way of an N-glycosyl link. This includes adenosine, cytidine, guanosine, uridine, thymidine, deoxyadenosine groups, and the like that may or may not carry specific hydroxy protecting groups. The term "amino acid group" means amino acid groups such as alanine, valine, glutamine, lycine, histidine, isoleucine, proline groups, and the like that may or may not carry specific hydroxy protecting groups. The term "steroidal groups" means groups containing a tetracyclyl cyclopenta[a]phenanthrene skeleton, such as aldosterone, androsterone, cholecalciferol, cholesterol, choleic acid, corticosterone, cortisol, cortisol acetate, cortisone, cortisone acetate, deoxycorticosterone, ergocalciferol, ergosterol, estradiol-17α, estradiol-17β, estriol, estrone, lanosterol, lithocholic acid, progesterone, testosterone, and the like that may or may not carry specific hydroxy protecting groups. The term "terpene group" means groups of unsaturated hydrocarbons having the formula $C_{10}H_{16}$, which are based upon the isoprene unit $C_5H_8$, which may be acyclics or cyclic with one or more benzenoid groups. This includes dipentene, pinene, mysene, menthane groups, and the like that may or may not carry specific hydroxy protecting groups. The term "oligonucleotide group" means a group typically containing 2–1000 nucleotides, and even larger polynucleotides. The term "nucleotide" means any compounds containing a heterocyclic compound bound to a phosphorylated sugar by an N-glycosyl link. Exemplary of such compounds are adenosine phosphate, flavin mononucleotide, and the like; but more specifically, the term also encompasses molecules which are combinations of a nucleic acid purine or pyrimidine, one sugar (usually ribose or deoxyribose), and a phosphate group, exemplary of such nucleotides would be adenylic acid, guanylic acid, uridylic acid, cytidylic acid, and the like that may or may not carry specific protecting groups. The term "phosphonopeptide" means a phosphorus-containing peptide derivative in which the carboxamide linkage between the two amino acids is replaced by a phosphono group. The term "phospholipid" means a bifunctional, trifunctional or multifunctional unit having a phosphorus group attached to one function and one or more long chain organic ($>C_6$) groups at the other functions and that may or may not include protecting groups. The term "phosphorus-containing polymer" means oligomers of greater than 5 units which contain phosphorus in the backbone or on the periphery of the backbone. The term "phosphonate-modified surface" means a glass, metal silicon, inorganic substrate, or other support having a phosphonate layer or multilayers with or without metals or other substrates in the layer or layers.

The trivalent phosphorus functional groups of the phosphorus-containing compounds can be selectively sulfurized. Alternatively, all of the trivalent phosphorus groups can be sulfurized. Furthermore, more than one phosphorus functional group can be sulfurized at a time, or they can be sulfurized sequentially (i.e., one at a time in a stepwise manner). For example, in the sulfurization of oligonucleotides it is desirable to sulfurize one nucleotide at a time. This prevents cleavage of the oligonucleotides when hydroxy protecting groups are removed by acidolysis.

For oligonucleotides, or other similar molecules, the sulfur-transfer reagents of Formula I and Formula II do not modify the nucleosidic residues, thereby preserving the genetic identity of the macromolecule. Thus, the reagents of Formula I and II and the method of the present invention can be reliably used in the automated synthesis of desired compounds. For example, the methodology has been proven for the automated synthesis on 0.2 to 1.0 μmol scales of oligonucleotides, including both oligodeoxyribonucleotides and oligoribonucleotides, of length 6 to 20 bases, containing the phosphorothioate substitution at either a single site or at all positions. It is envisioned that the methodology can be extended to DNA and RNA of 50 or more nucleotides in length. Such sulfur-containing oligonucleotides are potential therapeutics against HIV and other viral infections, for example.

Typically, an excess amount (e.g., 2–1000, preferably 2–200, and more typically, 25–30, molar equivalents) of the sulfur-transfer reagent of Formula I or Formula II is used relative to the amount of trivalent phosphorus groups in the phosphorus-containing compound. The reaction is typically carried out under an inert atmosphere, such as argon, although this is not required.

The sulfurization reaction occurs in a solvent. The solvent can be a hydrocarbon solvent, ethereal solvent, nitrile solvent, a chlorinated solvent, a heterocyclic solvent, etc. Specific examples of suitable solvents include pyridine, N,N-dimethylformamide (DMF), tetrahydrofuran (THF), acetonitrile ($CH_3CN$), methylene chloride ($CH_2Cl_2$), and the like. Preferably, the solvent is one in which both compounds are sufficiently soluble, or, in the case of solid-supported synthesis, which swells the resin-phosphorus compound conjugate sufficiently to allow the soluble compound of Formula I or II to access the phosphorus functionality, such that the reaction occurs in a reasonable amount of time.

Preferably, the reaction occurs in less than about 1 hour, more preferably in less than about 30 minutes, most preferably in less than about 15 minutes. In some applications, the reaction can be complete in as little as 30 seconds. Although it is desirable to carry out the reaction at room temperature (i.e., about 25°–30° C.), it can be carried out at a temperature within a range of about 0°–50° C., and preferably about 10°–50° C. Typically, the conversion of a compound of Formula III to the thioated derivative of Formula IV is greater than about 90%, and frequently greater than about 99%.

Although the inventors do not wish to be bound by theory or any mechanistic aspects of the reactions, the five-membered heterocycles of Formulas I and II are believed to react with trivalent phosphorus to effect sulfurization and produce COS. The reaction with DtsNH is also believed to form isocyanate, whereas the reaction with EDITH, is believed to form O-ethyl cyanates, for example. See Scheme 1, below, which represents proposed reaction mechanisms for the two reactions for peptides and DNA or RNA, for example. Although this scheme is specific for DtsNH and EDITH, it is also believed to be applicable to other sulfur-transfer reagents of Formulas I and II.

Scheme 1

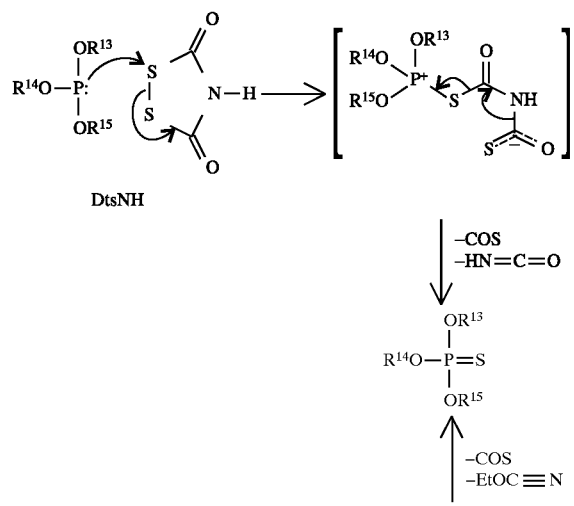

DtsNH

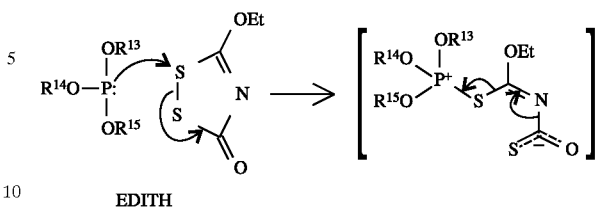

EDITH

In Scheme 1, for a peptide, $R^{13}$=Ser, Thr, Tyr, and $R^{14}$=$R^{15}$=allyl, t-butyl, benzyl, for example. For DNA and RNA, $R^{13}$ and $R^{14}$=dA, dC, dG, dT, A, C, G, U, and $R^{15}$=allyl, 2-cyanoethyl, methyl. Again Scheme 1 is not meant to be limiting with respect to the mechanism, sulfur transfer reagents, or compounds that can be sulfurized. It is meant only to be exemplary of what is believed to occur.

The reagents used in the methods of the present invention (DtsNH, EDITH, and related compounds of Formulas I and II) have an advantageous combination of properties that allow them to be useful alternatives to existing sulfurizing reagents. For example, they are easily prepared, easily handled (i.e., requiring no special handling precautions), and are stable (i.e., with no significant loss of activity) upon prolonged (e.g., several years) storage in solid form at about −20° C. and for several weeks in acetonitrile solution at room temperature. They are even stable in solid form at room temperature for at least about one year. They can be used at low concentrations (e.g., 0.05M) and for short reaction times (e.g., 30 seconds) with effective sulfur transfer efficiencies. Furthermore, they are soluble in a variety of organic solvents, such as acetonitrile, dichloromethane, nitromethane, chloroform, N,N-dimethylformamide, etc., which is important to prevent precipitation of the reagents when being used in the delivery and/or valve system of an instrument (e.g., automated synthesizer), thereby ensuring optimal performance of the device during synthesis. They also selectively and quantitatively react with the phosphorus-containing functionality of a compound.

The sulfur-transfer reagents of Formulae I and II are prepared in the Examples Section which follows. These compound preparations are considered illustrative of the preparation of other compounds encompassed by Formulas I and II, for example. As shown in Scheme 2, below, reaction of O-ethyl thiocarbamate with (chlorocarbonyl)sulfenyl chloride gives 3-ethoxy-1,2,4-dithiazoline-5-one (EDITH). EDITH is then converted with concentrated aqueous hydrochloric acid upon short reflux to 1,2,4-dithiazolidine-3,5-dione (DtsNH).

Scheme 2

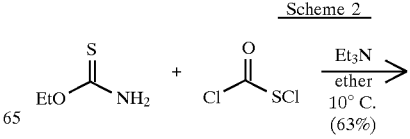

-continued
Scheme 2

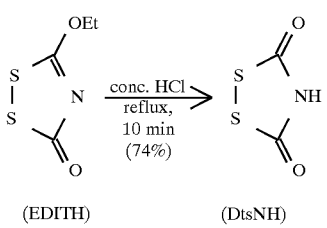

(EDITH)    (DtsNH)

The method of preparing EDITH using O-ethyl thiocarbamate and (chlorocarbonyl)sulfenyl chloride can result in undesirable side products, particularly a compound of the formula (Formula V):

The amount of this compound can be decreased, and the amount of EDITH increased, depending on the choice of solvent. For example, with an ethereal solvent, EDITH is the major product, whereas with a chlorinated solvent, the compound of Formula V is the major product. Thus, to enhance the formation of EDITH or other compounds of Formula II, the reaction is carried out in a nonhalogenated solvent. Examples of suitable nonhalogenated solvents include diethyl ether, methyl-t-butyl ether, tetrahydrofuran, toluene, 1,4-dioxane, and dimethoxyether. The solvent is chosen preferably such that the reactants are soluble. Preferably, the solvent is reasonably dry, although extreme precautions do not necessarily need to be taken for good yields of the compound of Formula II. Typically, the yield (isolated) of EDITH and other compounds of Formula II is prepared in greater than about 30% (and often in greater than 50%) when a nonhalogenated solvent is used.

The order of addition of reactants can also affect the yield. Preferably, the thioamide (e.g., thiocarbamate, dithiocarbamate, thiourea, etc.) is added to the (chlorocarbonyl)sulfenyl chloride for enhanced formation of compounds of Formula II. Also, the temperature can affect the yield. Preferably, the reaction is carried out at a temperature of no greater than about 20° C., and more preferably, no greater than about 10° C. Most preferably, the reaction is carried out in an ice bath. Advantageously, the reaction does not need to be carried out under an inert atmosphere. Typically, the yield of EDITH and other compounds of Formula II is prepared in greater than about 30% yield (isolated), and often greater than about 50% yield, when the temperature is no greater than about 20° C. and the above order of addition is used.

The invention will be further described by reference to the following detailed examples. These examples are offered to further illustrate the various specific and illustrative embodiments and techniques. It should be understood, however, that many variations and modifications may be made while remaining within the scope of the present invention.

EXAMPLES

General. $^1$H, $^{13}$C, and $^{31}$P NMR spectra were observed in the indicated deuterated solvents with an IBM NR 200 AF or NR 300 AF, or Varian VXR 300 instruments. $^1$H and $^{13}$C resonances are expressed as p.p.m. downfield from TMS; coupling constants of ethyl groups were approximately 7.1 Hz and are not specified. Exchanged protons are not reported. IR spectra were obtained on a Perkin Elmer 1600 Series FTIR spectrophotometer. Electron ionization mass spectra were obtained on a Finnigan MAT 95 instrument at the indicated eV and a source temperature of 200° C. Positive and negative methane chemical ionization mass spectra were recorded under the specified conditions on a Finnigan MAT 95 Mass Spectrometer. Low and high resolution fast atom bombardment mass spectroscopy (FABMS) were carried out on a VG Analytical 707E-HF low-resolution double-focusing mass spectrometer equipped with a VG 11/250 data system, operated at a resolution of 2000. Elemental analyses were performed by M-H-W Laboratories, Phoenix, Ariz.

Tetraethylthiuram sulfide (TETD) was from Applied Biosystems (Foster City, Calif.), and the Beaucage reagent was from Glen Research (Sterling, Va.). EDITH, m.p. 49°–51° C., and DtsNH, m.p. 141°–142° C., were both white needles prepared by procedures described below. Before use, acetonitrile solutions of DtsNH, EDITH, TETD, or the Beaucage reagent were placed over activated 4-Å molecular sieves for at least 12 hours. Eluents for chromatography were prepared using deionized water, solvents, and salts of the highest available grade. Reversed-phase high performance liquid chromatography (RP-HPLC) analyses of fully deprotected, crude synthetic oligonucleotides (DNA or RNA) containing single phosphorothioate linkages were performed using a Vydac analytical $C_{18}$ reversed-phase column (218TP54; 5 μm, 300 Å; 0.46×25 cm) on a Beckman system monitored at 260 nm. Separation of crude oligonucleotides that were fully sulfurized was achieved by ion-exchange HPLC using a Dionex NucleoPac PA-100 column (0.4×25 cm) as described in U.S. Pat. No. 5,395,928 to Bergot; Ausserer et al., *Biotechniques*, 19, 136–139 (1995), and B. Sproat et al., *Nucleosides and Nucleotides*, 14, 255–273 (1995). A PE-Sciex API III triple quadrupole mass spectrometer was used for electrospray mass spectrometry (ESMS) and a PerSeptive Biosystems linear mass spectrometer was used for matrix assisted laser desorption ionization (MALDI) to analyze oligonucleotides either directly after synthesis, or after HPLC fractionation. $^{31}$P Nuclear magnetic resonance (NMR) spectroscopy was used to analyze further phosphorothioate-containing oligonucleotides: fully deprotected material from 1.0 μmol scale syntheses was dissolved in 0.6 mL of $H_2O$, and spectra were recorded on a Varian VXR 300 MHZ NMR spectrometer operating at 121.4 MHZ, and referenced to external 85% phosphoric acid. $^{13}$C NMR spectra were recorded on the same Varian instrument operating at 75 MHZ.

EXAMPLE 1

Preparation of O-Ethyl Thiocarbamate

Solutions of potassium ethyl xanthate (192 g, 1.2 mol) in water (500 mL), and chloroacetic acid (113 g, 1.2 mol) and sodium hydroxide (48 g, 1.2 mol) in water (450 mL) were combined and stirred at 25° C. throughout a full working day, following which concentrated ammonium hydroxide (100 mL, about 1.5 mol) was added and stirring continued overnight. The product was then extracted into ethyl ether (2×500 mL), and the organic phase was washed with equal volumes of water and 1N aqueous HCl, dried ($MgSO_4$), and concentrated. The resultant oil was placed under petroleum ether at −20° C., providing a white solid. The purification process removed S-ethyl isomer which was present as a 7% contaminant in the crude product. Yield: 78.5 g (62%), m.p. 36°–38° C.; $^1$H NMR (CDCl$_3$) δ4.48 (q, 2 H), 1.34 (t, 3 H) [no δ2.9, diagnostic of S-ethyl isomer]; $^{13}$C NMR (CDCl$_3$) δ 192.0, 67.3, 13.8.

EXAMPLE 2

Preparation of 3-Ethoxy-1,2,4-dithiazoline-5-one ("EDITH")

Method A: A mixture of O-ethyl thiocarbamate (21.0 g, 0.2 mol), prepared as described above, and triethylamine (28 mL, 0.2 mol) in ethyl ether (100 mL) was added dropwise over 1 hour into a stirred and externally chilled solution of (chlorocarbonyl)sulfenyl chloride (16.8 mL, 0.2 mol, prepared according to Barany et al., *J. Org. Chem.,* 48, 4750–4761 (1983) in ethyl ether (1 L), at a rate to maintain the reaction temperature below 10° C. After an additional 4.5 hours of stirring, the precipitated triethylamine hydrochloride (30.2 g, quantitative) was removed by filtration. The filtrate was concentrated to provide a light-yellow solid (26.8 g, 91% purity by $^1$H NMR). Recrystallization from ether (100 mL) at −20° C. gave off-white needles (16.4 g), m.p. 51°–53° C. The mother liquor provided an additional portion of light yellow needles (4.1 g), m.p. 42°–46° C. Total yield: 20.5 g (63%).

Method B: A solution of O-ethyl thiocarbamate (5.25 g, 0.05 mol), prepared as described above, in ethyl ether (25 mL) was added dropwise over 40 minutes into a stirred and externally chilled solution of (chlorocarbonyl)sulfenyl chloride (4.2 mL, 0.05 mmol) in ethyl ether (250 mL), at a rate to maintain the reaction temperature below 10° C. A white precipitate formed but disappeared as the reaction progressed with an additional 1.5 hours of stirring at 25° C. Solvent was evaporated at reduced pressure, and the residue was redissolved in CH$_2$Cl$_2$ (100 mL), filtered to remove an insoluble white solid (0.4 g) believed to be cyanuric acid (2,4,6-trihydroxy-1,3,5-triazine), and reconcentrated to provide a light-yellow solid (7.22 g, 89% purity by $^1$H NMR). Recrystallization from ether (15 mL) at −20° C. gave off-white needles (3.6 g). The mother liquor provided an additional portion of light yellow needles (0.6 g). Total yield: 4.2 g (52%).

Characterization of 3-ethoxy-1,2,4-dithiazoline-5-one. $^1$H NMR (CDCl$_3$) δ4.68 (q, 2 H), 1.47 (t, 3 H); $^{13}$C NMR (CDCl$_3$) δ187.3, 179.6, 73.5, 14.1; IR (CDCl$_3$): 2990 (w), 1705 (s), 1541 (vs), 1470 (m), 1393 (w), 1365 (w), 1297 (w), 1259 (s), 1239 (m), 1153 (w), 1004 (w) cm$^{-1}$; positive methane CIMS (source 160° C., solid probe 20° C., 0.1 mm): m/z 164 [(M+1)$^+$, 100%], 136 [(M+1)$^+$—CO, 67%]; negative methane CIMS m/z 162 [(M$^+$−1), 59%], 133 (14%), 102 [(M−1)$^-$—COS, 100%]; EIMS (source 200° C., solid probe 30° C.): m/z 163 (M+, 24%), 135 (M$^+$—CO, 13%), 131 (M$^+$−S, 10%), 107 (M$^+$—CO—C$_2$H$_4$, 18%), 103 (M$^+$—COS, 8%), 70 (79%), 64 (29%), 60 (21%), 29 (C$_2$H$_5$$^+$, 100%). Analysis calculated for C$_4$H$_5$NO$_2$S$_2$ (mol wt 163.22): C, 29.44; H, 3.09;N, 8.58; S, 39.29. Found: C, 29.23; H, 3.14;N, 8.68; S, 39.41. Samples of crystalline EDITH were maintained under ambient conditions, exposed to open atmosphere, for up to 2 years without any signs of decomposition as judged by $^1$H NMR, $^{13}$C NMR, and m.p. redetermination; routine storage is carried out at −20° C.

EXAMPLE 3

Preparation of 1,2,4-Dithiazolidine-3,5-dione ("DtsNH")

A stirred suspension of recrystallized 3-ethoxy-1,2,4-dithiazoline-5-one (13.9 g, 85 mmol), prepared as described above, in concentrated aqueous HCl (80 mL) was brought to a temperature of 110° C. over a 45 minute period. Ten minutes after the suspension reached this temperature, it was passed while hot through a glass fritted funnel to remove elemental sulfur. The filtrate was concentrated to dryness to provide a solid which was crystallized from toluene. Yield: 8.5 g (74%), m.p. 141°–143° C.; $^{13}$C NMR (CDCl$_3$) δ167.7; $^{13}$C NMR (CD$_3$CN) δ168.7; IR (CDCl$_3$) 3360 (w), 1735 (s), 1700 (vs), 1683 (s, sh), 1287 (m) cm$^{-1}$; methane CIMS (source 160° C., solid probe 60° C., 0.1 mm): m/z 136 [(M+1)$^+$, 100%], 108 [(M+1)$^+$—CO, 29%], 93 (14%), 64 (S$_2$$^+$, 19%). Analysis calculated for C$_2$HNO$_2$S$_2$ (mol wt 135.16): C, 17.77; H, 0.74; N, 10.36; S, 47.44. Found: C, 17.91; H, 0.84;N, 10.44; S, 47.31. Samples of crystalline DtsNH were maintained under ambient conditions for 2 years or more without any signs of decomposition as judged by $^{13}$C NMR, repeat elemental analysis and mp redetermination; routine storage is carried out at −20° C.

EXAMPLE 4

Preparation of 3-Methyl-1,2,4-dithiazoline-5-one

A mixture of thioacetamide (0.73 g, 10 mmol) and triethylamine (2.8 mL, 20 mmol) in 1,2-dimethoxyethane (5 mL) was added dropwise over 20 minutes into a stirred and externally chilled solution of (chlorocarbonyl)sulfenyl chloride (0.84 mL, 10 mol, prepared according to Barany et al., *J. Org. Chem.,* 48, 4750–4761 (1983)) in 1,2-dimethoxyethane (50 mL), at a rate to maintain the reaction temperature below 10° C. After an additional 1 hour of stirring, the precipitated triethylamine hydrochloride was removed by filtration. The filtrate was concentrated at reduced pressure to provide a dark-brown solid (0.9 g). The crude product was mixed with ethyl acetate (6 mL), and ⅔ of the solution was applied to flash chromatography (hexane:ethyl acetate=4:1) to produce off-white solid. Total yield: 0.29 g (29%); m.p. 64°–67° C. $^1$H NMR (CDCl$_3$) δ2.73 (s, 3 H); $^{13}$C NMR (CDCl$_3$) δ192.7, 188.0, 23.1. Anal. calculated for C$_3$H$_3$NOS$_2$ (mol wt 103.18): C, 27.06; H, 2.27;N, 10.52; S, 48.14, found: C, 26.88; H, 2.20;N, 10.66; S, 48.12.

EXAMPLE 5

Stabilities of DtsNH and EDITH

To determine the stabilities and solubilities of DtsNH and EDITH upon prolonged storage in solution, 0.2M and 0.05M solutions were prepared in CH$_3$CN and stored at 25° C. over 4-Å molecular sieves. During a 2 week period, these solutions were tested periodically by RP-HPLC analysis [C$_{18}$ column developed at 1.2 mL/minute with 0.1% aqueous TFA-CH$_3$CN from 19:1 to 3:2 over 12 minutes, monitored at 254 nm]. At both concentrations tested, the only peaks observed were those of the compounds under evaluation, and the peak areas remained entirely unchanged. In addition, $^{13}$C NMR and $^1$H NMR spectra in CD$_3$CN were recorded after one month and compared to those of freshly prepared solutions: no new peaks appeared. Moreover, the solutions remained clear and colorless over 2 weeks. The solubility of the Beaucage reagent as a 0.05M solution in CH$_3$CN was evaluated similarly: already after 2 days, a significant precipitate occurred even when silanized bottles were used according to the manufacturer's recommendations.

The sulfurization efficiency of freshly prepared EDITH and DtsNH (0.05M solution and 30 seconds reaction time) was compared to that of 2-month and 1-month old solutions, respectively, in the synthesis of 5'-d(TTT$_S$TTA)-3'. RP-HPLC analysis of crude product oligomers indicated that in all cases >98% sulfur transfer efficiency was achieved. It is also worth comparing the favorable properties of DtsNH and EDITH found here with those described for S-Tetra, which gives inferior oligonucleotide synthesis results with solutions stored more than 1 week as disclosed in Stec et al., Tetrahedron Lett., 34 5317–5320 (1993).

EXAMPLE 6

Solid-phase Synthesis of Phosphorothioate-Containing Oligodeoxyribonucleotides

A Pharmacia Gene Assembler Special DNA/RNA Synthesizer was operated on either a 0.2 μmol or 1.0 μmol scale, starting with controlled pore-glass (500 Å) supports loaded with the 3'-end deoxyA residue attached to the supports via a long chain alkylamino linker (dA-lcaa-CPG), and using β-cyanoethyl deoxyribonucleoside phosphoramidites and other standard solvents and reagents (all from Glen Research, Sterling, Va.). Conditions used for sulfurization are described in Tables 1 and 2. The typical sulfurizing reagent volume used per cycle was 1.25 mL, regardless of the synthesis scale chosen. However, identical results were achieved with 0.5 mL. The sulfurizing reagent was recycled through the column at a flow rate of 2.5 mL/minute during the reaction times indicated in Tables 1 and 2. The capping step in the synthesis cycle was performed after the sulfurization reaction, in order to avoid premature oxidation of the phosphite linkage. The remaining steps in the synthesis cycle were performed according to standard methods for the Pharmacia Gene Assembler Special DNA/RNA Synthesizer. Upon completion of solid-phase steps, the oligodeoxyribonucleotides were released from the support and deblocked with 30% ammonium hydroxide (15 hours, 55° C.), desalted on $C_{18}$ Sep-Pak cartridges (Millipore), lyophilized, and analyzed by reversed-phase and/or ion-exchange HPLC, polyacrylamide gel electrophoresis, ESMS, and $^{31}P$ NMR.

Synthesis of an Oligodeoxyribonucleotide Hexamer Containing a Single Internal Phosphorothioate Linkage: The product phosphorothioates were formed as a mixture of two stereoisomers. Reversed-phase HPLC analysis was conducted for the oligodeoxyribonucleotide hexamer 5'-d(TTT$_S$TTA)-3' synthesized on a 0.2 μmol scale, with the single phosphorothioate linkage established by 30 second reaction with 0.05M DtsNH in $CH_3CN$. Chromatograms were developed at 1.2 mL/minute with 0.1M aqueous triethylammonium acetate (TEAA) pH 7.0 buffer: a gradient starting from 92% buffer and 8% $CH_3CN$ was increased over 20 minutes by 0.4% $CH_3CN$/minute. The $R_p$ diastereomer was at $t_R$=16.4 minute, and the $S_p$ diastereomer was at $t_R$=17.6 minute. See also Table 1.

In addition, there is the possibility of forming an undesired by-product containing a phosphodiester linkage—due to incomplete sulfurization and/or some side reaction related to the reagent used. Sulfurization yields for the singly-sulfurized species were determined by elution of crude oligomers on RP-HPLC. Excellent yields (>98%) of the desired phosphorothioate triesters were observed when 0.05M DtsNH (Table 1, lines 1 and 2) or 0.05M EDITH (Table 1, line 5) were applied for 30 to 60 seconds. The Beaucage reagent was also effective under the same conditions (Table 1, lines 6 and 7). However, at the lower concentration of 0.01M, 5 minute reaction times were needed for both the DtsNH and Beaucage reagents to achieve the same sulfurization yields (Table 1, lines 3 and 8 vs. lines 4 and 9). In contrast, the maximum sulfurization achievable by TETD (about 96%) required 0.5M concentration and a 15 minute reaction time (Table 1, line 10).

TABLE 1

Sulfur-transfer Efficiency of Various Reagents for Synthesis of the Hexamer 5'-d(TTT$_S$TTA)-3'

| Sulfurizing Reagent | Concentration $CH_3CN$ (M) | Reaction Time (min) | Distribution (%) | | |
|---|---|---|---|---|---|
| | | | 1 (P=O) | 2 (P=S$_R$) | 3 (P=S$_S$) |
| DtsNH | 0.05 | 1.0 | <2 | 56 | 42 |
| DtsNH | 0.05 | 0.5 | <2 | 56 | 42 |
| DtsNH | 0.01 | 5.0 | <2 | 56 | 42 |
| DtsNH | 0.01 | 1.0 | 7 | 53 | 40 |
| EDITH | 0.05 | 0.5 | <2 | 56 | 42 |
| Beaucage | 0.05 | 1.0 | <2 | 56 | 42 |
| Beaucage | 0.05 | 0.5 | <2 | 55 | 44 |
| Beaucage | 0.01 | 5.0 | <2 | 55 | 42 |
| Beaucage | 0.01 | 1.0 | 19 | 44 | 36 |
| TETD | 0.5 | 15.0 | 4 | 52 | 44 |

Hexamers were synthesized on a 0.2 μmol scale, with the single phosphorothioate linkage established by using reaction times and concentrations of sulfurization reagent as indicated. Relative distributions reported were determined by HPLC analysis. Chromatograms were developed at 1.2 mL/minutes with 0.1M aqueous triethylammonium acetate (TEAA) pH 7.0 buffer: a gradient starting from 92% buffer and 8% $CH_3CN$ was increased over 20 minutes by 0.4% $CH_3CN$/minutes. Peaks 1, 2, and 3 were assigned as follows, based on isolation followed by ESMS: 1, 5'-d(TTTTTA)-3', $t_R$=15.4 minutes, m/z=1772.4; 2, 5'-d(TTT$_{s(R)}$TTA)-3', $t_R$=16.4 minutes, m/z=1788.8; 3, 5'-d(TTT$_{s(S)}$TTA)-3', $t_R$=17.6 min, m/z=1788.3.

Syntheses of Oligodeoxyribonucleotide Hexamers Containing Multiple Phosphorothioate Linkages: Oligodeoxyribonucleotide hexamers (two different sequences) were prepared containing a phosphorothioate diester at every position. This was achieved by carrying out the sulfurization reactions after each of the coupling cycles during automated chain assembly. See Table 2.

TABLE 2

Sulfur-transfer Efficiency of Various Reagents for Syntheses of Oligodeoxyribonucleotide Hexamers

| Sulfurizing Reagent | Sequence* | Concentration in $CH_3CN$ (M) | Reaction Time (min) | Distribution (%) | |
|---|---|---|---|---|---|
| | | | | P=S | P=O |
| DtsNH | i | 0.05 | 0.5 | ~100 | N.D. |
| DtsNH | i | 0.01 | 5.0 | 97 | 3 |
| EDITH | i | 0.05 | 0.5 | ~100 | N.D. |
| Beaucage | i | 0.05 | 0.5 | ~100 | N.D. |
| Beaucage | i | 0.01 | 5.0 | 97 | 3 |
| DtsNH | ii | 0.05 | 0.5 | ~100 | N.D. |
| EDITH | ii | 0.05 | 0.5 | ~100 | N.D. |
| Beaucage | ii | 0.05 | 0.5 | ~100 | N.D. |

*(i) 5'-d(T$_S$T$_S$T$_S$T$_S$T$_S$A)-3'; (ii) 5'-d(G$_S$A$_S$C$_S$G$_S$T$_S$A)-3'
Hexamers were synthesized on a 1.0 μmol scale, with the five phosphorothioates each established by reaction times and sulfurization reagent concentrations as indicated. Relative amounts of P=S (δ 56 ppm) and P=O (δ~0 ppm) were determined by integration of the $^{31}P$ NMR spectra.

31P NMR analysis revealed that, within the resolution of the technique, all three reagents, DtsNH, EDITH, and the Beaucage reagent are effective for sulfurization. When the concentration of sulfurizing reagent was 0.05M, no phosphodiester linkage could be detected by $^{31}P$ NMR. For example, $^{31}P$ NMR of the oligodeoxyribonucleotide hexamer 5'-d(T$_S$T$_S$T$_S$T$_S$T$_S$A)-3' synthesized on a 1.0 μmol scale, with the five phosphorothioates established by 30 second reactions with 0.05M DtsNH in $CH_3CN$ at each cycle of chain elongation. A single peak was observed at δ55.9 ppm. If present, a phosphodiester resonance is expected around δ0 ppm.

Syntheses of Oligodeoxyribonucleotide 20-mers Containing Multiple Phosphorothioate Linkages: The suitability of these reagents for the automated solid-phase synthesis of longer phosphorothioate-containing oligodeoxyribonucleotide analogues was evaluated. Two sets of oligodeoxyribonucleotide 20-mers containing a phosphorothioate diester at every position were prepared. $^{31}P$ NMR analysis of S-d $(T_{19}A)$ prepared using 0.05M of the Beaucage reagent or EDITH (e.g., FIG. 1) and 30 second reaction times indicated that on average greater than 99% sulfur transfer efficiency was achieved at each step. A comparison of the crude products obtained with these two reagents was carried out using polyacryamide gel electrophoresis. Comparable ratios of full-length to truncated product oligomers were obtained. DtsNH, on the other hand was not as effective for sulfurization of these longer sequences. However, at higher concentrations of reagent (0.2M) and longer reaction times (5 minutes), greater than 99% sulfur transfer efficiency was achieved as revealed by $^{31}P$ NMR analysis (data not shown). Gel analyses showed that the percentage of full-length product oligomers obtained when DtsNH was used was similar to that from syntheses carried out with EDITH or the Beaucage reagent.

Figure 2A:
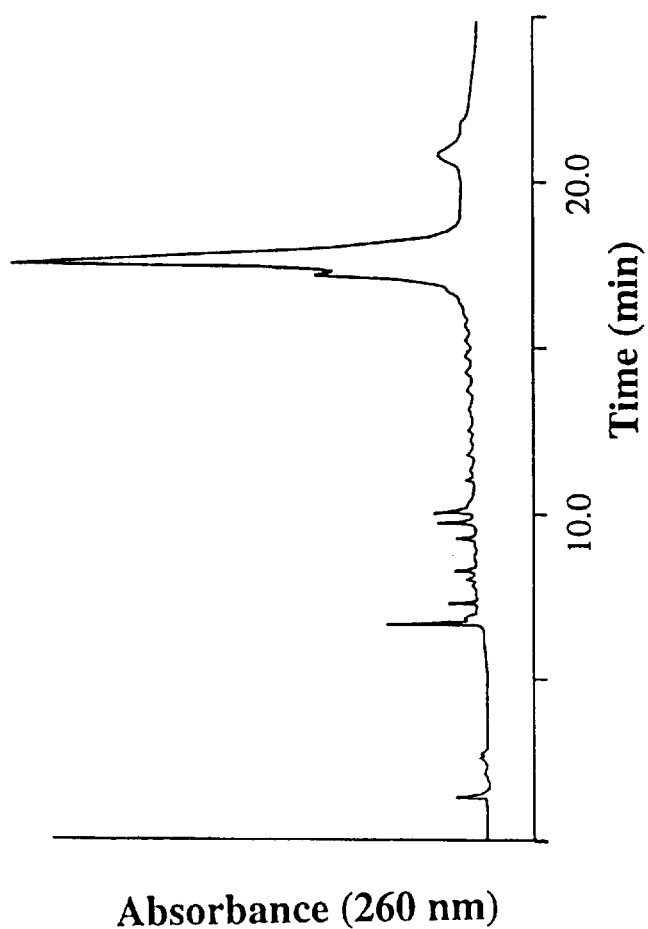
FIG. 2. Anion-exchange HPLC at 55° C. of oligodeoxyribonucleotide S-d($T_{19}$A) synthesized on a 1.0 μmol scale, with multiple phosphorothioate linkages established by 30 second reactions with 0.05M sulfurizing reagent in $CH_3CN$. Elution was at 1.2 mL/minute by a gradient starting from 100% buffer A=20 mM Tris-HCl, pH 8.0-$CH_3CN$ (10:1) increased over 20 minutes by 2%/minute of buffer B=0.8M $NaClO_4$—$CH_3CN$ (10:1). (A) Sulfurizations performed by EDITH; (B) Sulfurizations performed by the Beaucage reagent.
Figure 2B:
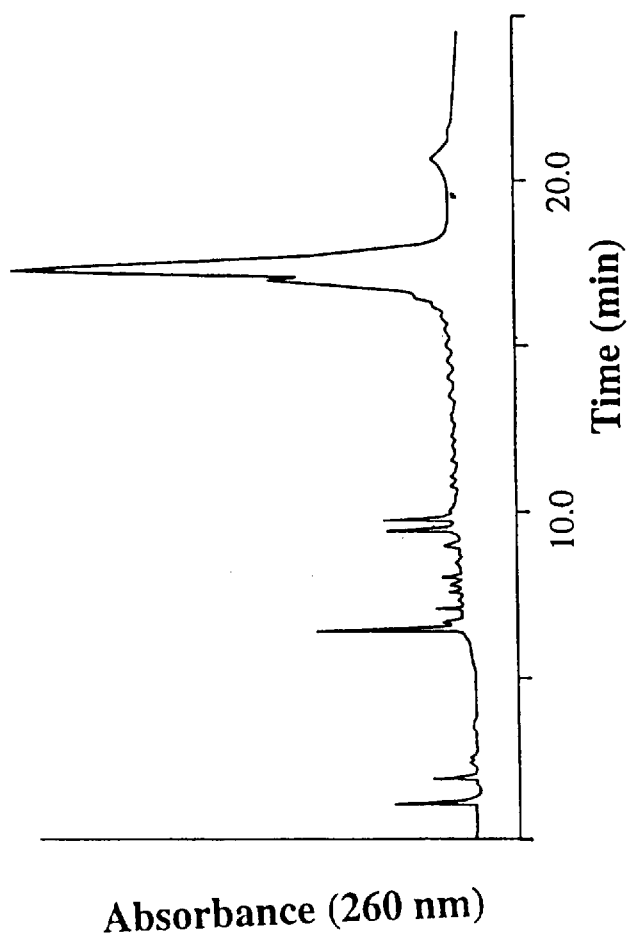

One can readily calculate that for the synthesis of a 20-mer, even if only 1% of phosphite precursors were oxygenated instead of sulfurized, 16.5% of the products would be expected to contain one phosphodiester linkage. To determine the percentage of crude product that was not the desired fully-sulfurized oligomer, a literature procedure (U.S. Pat. No. 5,395,928 to Bergot; Ausserer et al., *Biotechniques*, 19, 136–139 (1995), and B. Sproat et al., *Nucleosides and Nucleotides*, 14, 255–273 (1995)) was adapted whereby strong anion-exchange HPLC separates fully sulfurized phosphorothioate oligonucleotides from incompletely sulfurized species. Crude product oligomers of S-d($T_{19}$A), sulfurized with EDITH and the Beaucage reagent, were chromatographed by this technique (FIG. 2). The major peaks correspond to the fully sulfurized product, and the small shoulder peaks are believed to be the singly-oxidized species. Thus, the product distribution observed by anion-exchange chromatography shows that the sulfur transfer efficiency is indeed greater than 99% at each step, and confirms the NMR results.

Figure 3A:
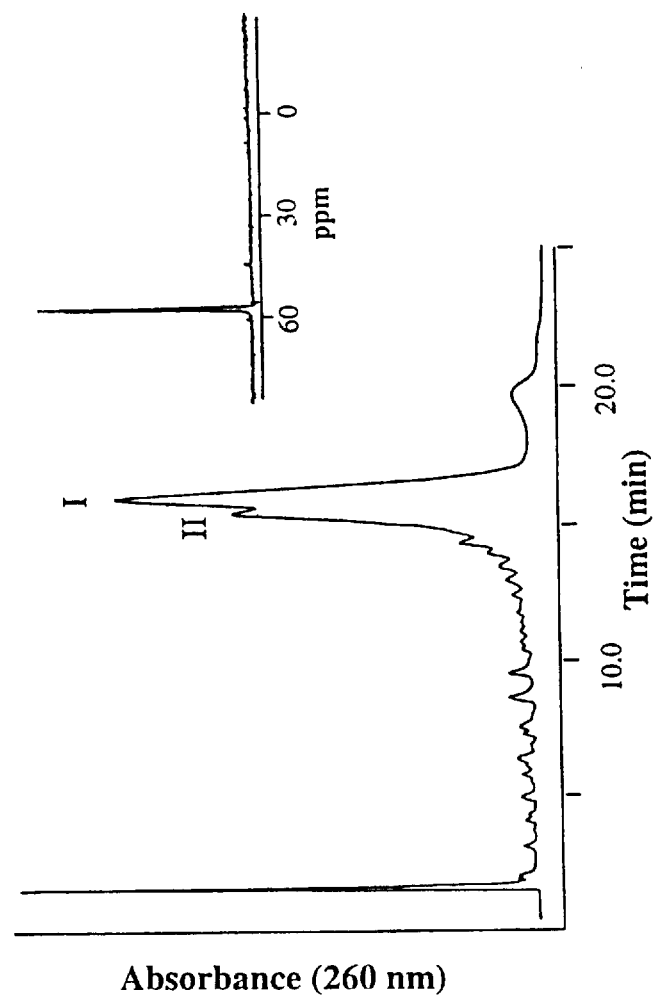
FIG. 3. Both anion-exchange HPLC (conditions of FIG. 2) and $^{31}$P NMR (insets) of the oligodeoxyribonucleotide S-d(CCTCTTCGCTATTACGCCAA) synthesized on a 1.0 μmol scale, with multiple phosphorothioate linkages established by 30 seconds reactions with 0.05M sulfurizing reagent in $CH_3CN$. (A) Sulfurizations performed by EDITH; (B) Sulfurizations performed by the Beaucage reagent.
Figure 3B:
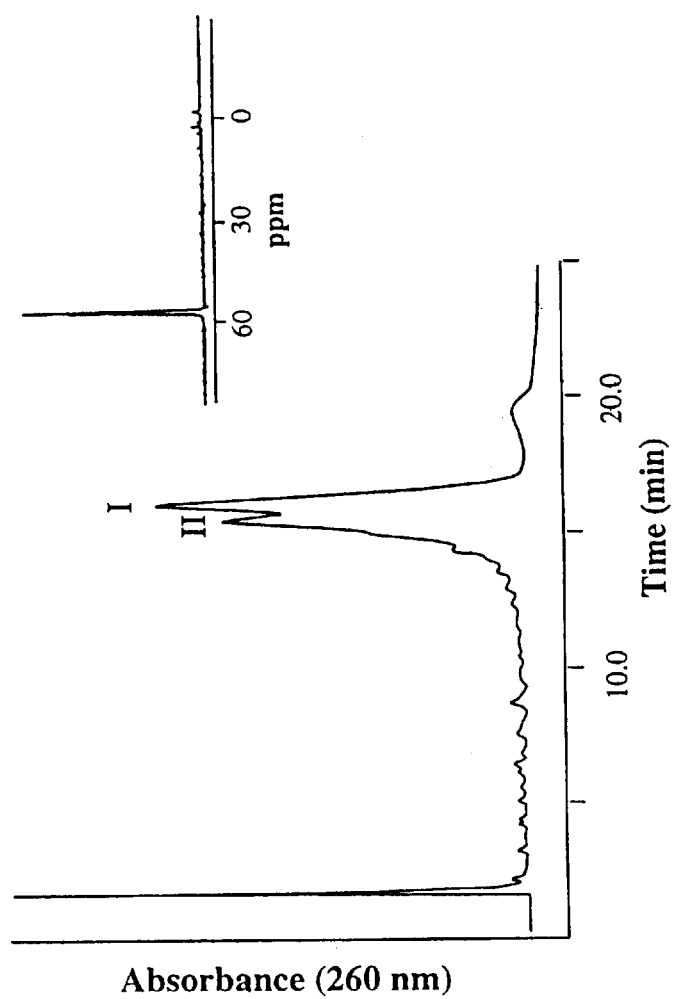

A mixed 20-mer oligodeoxyribonucleotide S-d (CCTCTTCGCTATTACGCCAA) was also synthesized, using both EDITH and the Beaucage reagent at 0.05M and 30 sec reaction times. $^{31}P$ NMR again revealed that approximately 98-99% sulfur transfer efficiency was achieved at each step. Anion-exchange chromatography of the crude product oligomers showed that the major species was the full-length, fully sulfurized desired product (FIG. 3). The relative heights of peak II's suggests that both reagents are somewhat less effective at sulfurizing the mixed sequence 20-mers than was the case for the preparations of S-d($T_{19}$A) (FIG. 2). For a 20-mer, a 2% yield of oxygenated product at each step would result in 59% fully-sulfurized product. The anion-exchange results are therefore consistent with the stepwise sulfur transfer efficiency estimated by NMR. Gel analysis of the mixed sequences was also carried out and the results confirm that comparable yields of full-length and truncated products were obtained with EDITH and the Beaucage reagent.

EXAMPLE 7

Solid-Phase Synthesis of Phosphorothioate-Containing Oligoribonucleotides

A Pharmacia Gene Assembler Special DNA/RNA Synthesizer was operated on a 1.0 μmol scale, starting with controlled pore-glass (500 Å) supports loaded with the 3'-end riboA residue attached to the supports via a long chain alkylamino linker (A-lcaa—CPG), (Glen Research, Sterling, Va.) and using β-cyanoethyl ribonucleoside phosphoramidites (ChemGenes, Waltham, Mass.) and other standard solvents and reagents (Glen Research, Sterling, Va.). A new activator, 5-ethylthio-1H-tetrazole (available from American International Chemical, Inc., Natick, Mass., and Glen Research, Sterling, Va.), which has greater acidity and solubility in acetonitrile than tetrazole, was used for the coupling. Conditions used for sulfurization are described in Table 3. The typical sulfurizing reagent volume used per cycle was 1.25 mL. The sulfurizing reagent was recycled through the column at a flow rate of 2.5 mL/minute during the reaction times indicated in Table 3. The capping step in the synthesis cycle was performed after the sulfurization reaction, in order to avoid premature oxidation of the phosphite linkage. The remaining steps in the synthesis cycle were performed according to standard RNA methods for the Pharmacia Gene Assembler Special DNA/RNA Synthesizer. Removal of the oligoribonucleotides from the polymer support was accomplished by incubation at 55° C. for 24 hours in ethanolic ammonia. The supernatant of this reaction mixture was evaporated to dryness and the silyl protecting groups were removed with neat triethylamine trihydrofluoride (24 hours, 25° C.) as described in B. Sproat et al., *Nucleosides and Nucleotides*, 14, 255–273 (1995). To recover the oligoribonucleotide from the above solution, excess 1-butanol was added. The mixture was chilled at −20° C. overnight (6-mer) or for at least two hours (20-mer). The tube was centrifuged at 5000 r.p.m. for 5 minutes and the butanol decanted to collect the precipitated RNA. RNA oligonucleotides were dissolved in DEPC-treated (DEPC= diethylpyrocarbonate) water prior to analysis.

Analysis of Fully Deprotected RNA: Separation of crude oligoribonucleotides that were fully sulfurized was achieved by ion-exchange HPLC using a Dionex NucleoPac PA-100 column (0.4×25 cm) as described in Sproat et al., *Nucleosides and Nucleotides*, 14, 255–273 (1995). A two-eluent system was used: A, 20 mM $LiClO_4$/20 mM NaOAc-HOAc, pH=6.5-$CH_3CN$ (10:1); and B, 800 mM $LiClO_4$/20 mM NaOAc-HOAc, pH 6.5—$CH_3CN$ (10:1). Eluents were prepared using deionized water and salts of the highest available grade. Analyses were performed on oligoribonucleotides synthesized trityl-off by heating the analytical column to 60° C. to minimize RNA secondary structural effects. Reversed-phase high performance liquid chromatography (RP-HPLC) analyses of fully deprotected, crude synthetic oligoribonucleotides containing single phosphorothioate linkages was performed using a Vydac analytical $C_{18}$ reverse-phase column (218TP54; 5 μm, 300 Å; 0.46×25 cm) on a Beckman system monitored at 260 nm. A two-eluent system was used: A, 0.1M TEAA pH 7.0; and B, 80% $CH_3CN$ in 0.1M TEAA. $^{31}P$ NMR spectroscopy was also used to analyze phosphorothioate-containing oligoribonucleotides: fully deprotected material from 1 μmol scale synthesis was dissolved in 0.6 mL of DEPC-treated water, and spectra were recorded on a Varian VXR 300 MHz NMR spectrometer, and referenced to external 85% phosphoric acid.

Figure 4A:
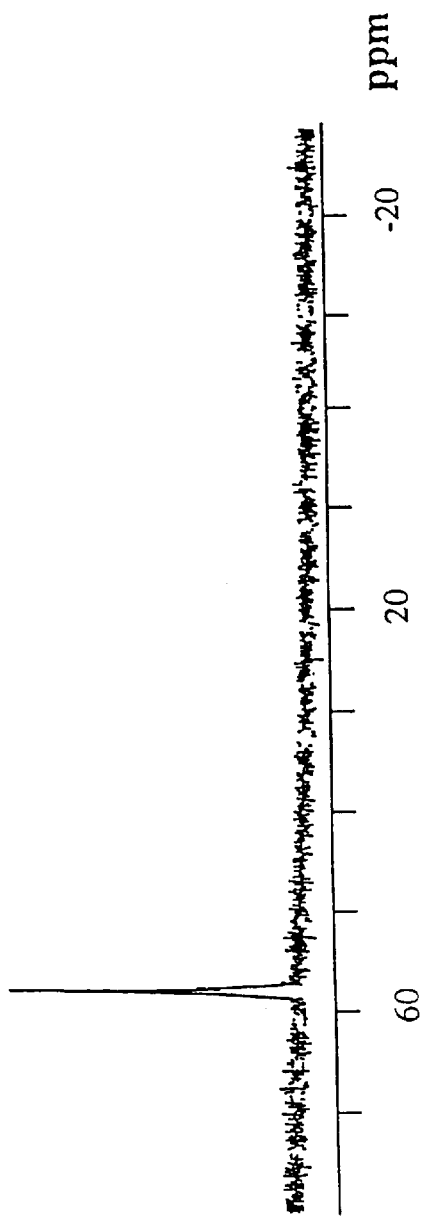
FIG. 4. $^{31}$P NMR containing a major peak at δ57.7 ppm of the oligoribonucleotide hexamer 5'-$U_sU_sU_sU_sU_s$A-3' with multiple phosphorothioate linkages. (A) sulfurization reaction was performed by 2 minute reaction time with 0.05M EDITH in acetonitrile; (B) sulfurization reaction was performed by 2 minute reaction time with 0.05M the Beaucage reagent in acetonitrile; and (C) sulfurization reaction was performed by 5 minute reaction time with 0.2M DtsNH in acetonitrile.
Figure 4C:
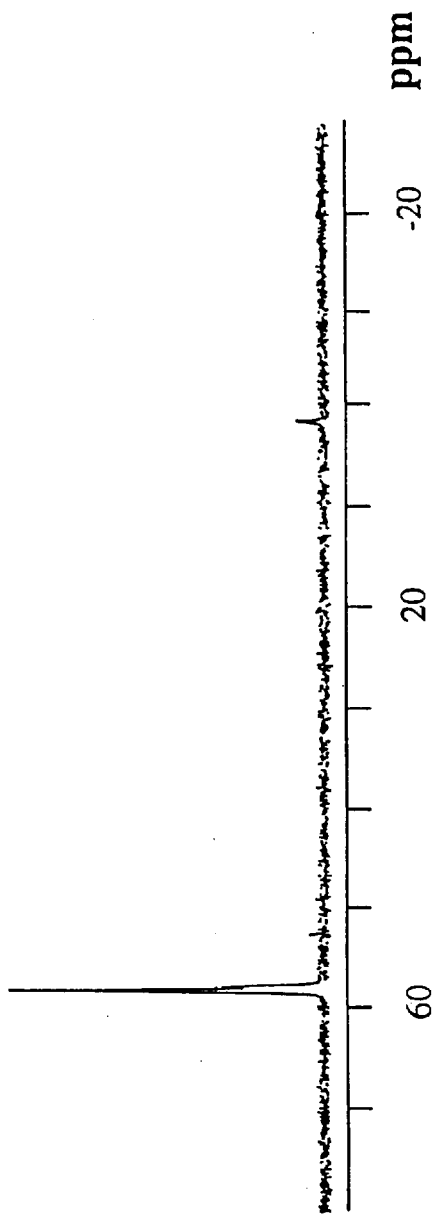

Synthesis of Oligoribonucleotides Containing Single or Multiple Internal Phosphorothioate Linkages: $^{31}P$ NMR analysis indicates that nearly quantitative sulfurization yields were obtained for all sequences prepared with 0.05M EDITH and 2.0 minute reaction times (Table 3, lines 2, 4, 7, 9, and 10). FIGS. 4A, 4B, and 4C show a comparison of the NMR spectra obtained when the same sequence (S-$U_5$-A) was prepared with three different sulfurization reagents (DtsNH, EDITH, and the Beaucage reagent). The Beaucage reagent and DtsNH appear to be less effective than EDITH at sulfurizing an RNA hexamer. These results were con- In summary, EDITH is more effective than the Beaucage reagent or DtsNH in the automated synthesis of phosphorothioate-containing RNA oligonucleotides of length 6 to 20 nucleotides. Moreover, in this application EDITH can be used at low concentrations (0.05M) and with short reaction times (2 minutes) and results in nearly quantitative sulfur transfer at each step.

TABLE 3

Sulfurization of RNA Oligonucleotides by Different Reagents

Figure 5A:
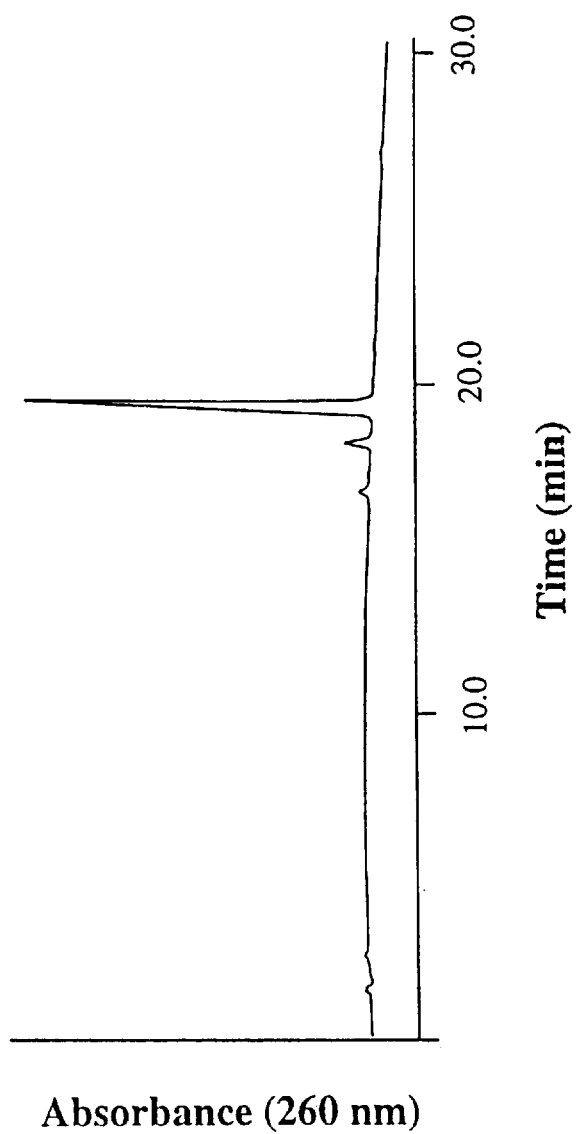
FIG. 5. Anion-exchange HPLC of the oligoribonucleotide hexamer 5'-$U_sU_sU_sU_sU_s$A-3' containing multiple phosphorothioate linkages. Chromatograms were developed at 1.2 mL/min: a gradient starting from 100% eluent A (20 mM $LiClO_4$/20 mM NaOAc-HOAc, pH 6.5-$CH_3CN$ (10:1)) and 0% eluent B (800 mM $LiClO_4$/20 mM NaOAc-HOAc, pH 6.5-$CH_3CN$ (10:1)) was increased over 18 minutes by 2.8% eluent B/minute. Peak 1 is the product with one oxygen in place of sulfur ($t_R$=18.0 minutes), and peak 2 is the fully-sulfurized product ($t_R$=19.0 minutes). (A) Sulfurization reaction was performed by 2 minute reaction time with 0.05M EDITH in acetonitrile; (B) sulfurization reaction was performed by 2 minute reaction time with 0.05M of the Beaucage reagent in acetonitrile; and (C) sulfurization reaction was performed by 5 minute reaction time with 0.2M DtsNH in acetonitrile.
Figure 5C:
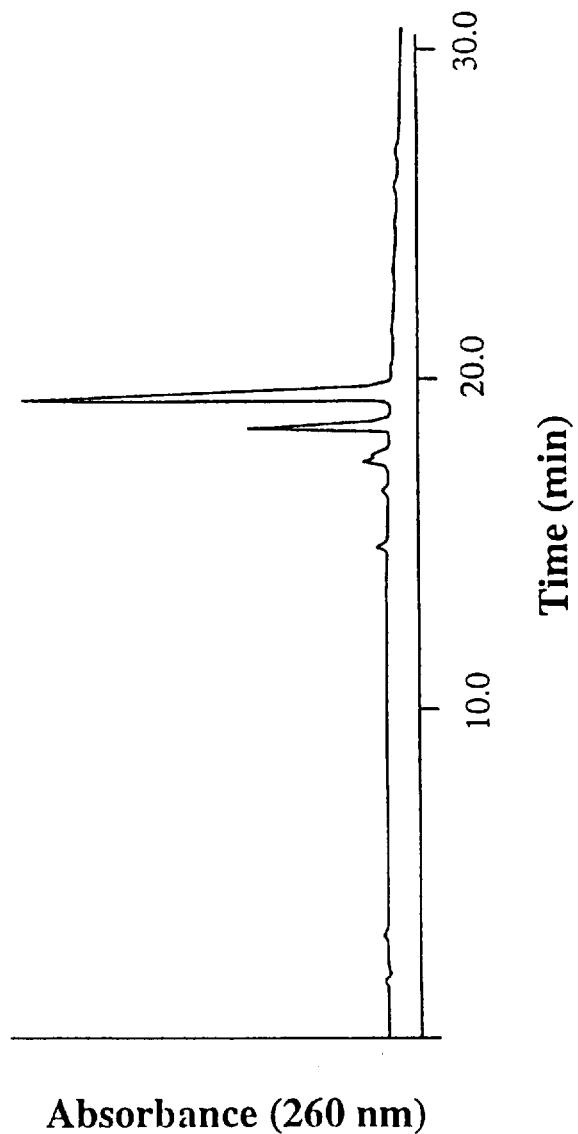

| | | | $^{31}$P NMR | | HPLC | |
|---|---|---|---|---|---|---|
| | | | | | %1 P=O | % all P=S |
| Reagent | Conc. (M)/ Time (min) | RNA sequence | % P=O | % P=S | (18.0 min) | (19.0 min) |
| DtsNH | 0.20/5.0 | S-$U_5$A | 4 | 96 | 21.1 | 70.0 |
| EDITH | 0.05/2.0 | S-$U_5$A | N.D. | >99 | 5.5 | 91.8 |
| Beaucage | 0.05/2.0 | S-$U_5$A | 1 | ~99 | 13.1 | 84.4 |
| EDITH | 0.05/2.0 | S-$U_{19}$A | N.D. | >99 | 5.6 | 94.3 |
| Beaucage | 0.05/2.0 | S-$U_{19}$A | 2 | 98 | 27.5 | 70.7 |
| Beaucage | 0.05/2.0 | i | 5 | 95 | N.D. | N.D. |
| EDITH | 0.05/2.0 | i | N.D. | >99 | N.D. | N.D. |
| Beaucage | 0.05/2.0 | ii | 96 | 4 | N.D. | N.D. |
| EDITH | 0.05/2.0 | ii | 95 | 5 | N.D. | N.D. |
| EDITH | 0.05/2.0 | iii | 95 | 5 | N.D. | N.D. | i: 5'-$A_S A_S U_S C_S C_S U_S C_S U_S C_S U_S C_S G_S C_S C_S G_S A_S C_S C_S$A-3'
ii: 5'-AAUCCUCUCUCGCC$_S$GACCA-3'
iii: 5'-AAUCCUC$_S$UCUCGCCGACCA-3'
N.D.: No Data firmed by anion exchange chromatography (FIG. 5), wherein the amount of product containing a singly oxygenated species can be quantified. Reaction with EDITH resulted in only 5.5% of this undesired product (FIG. 5A), confirming a greater than 99% sulfurization efficiency. Higher yields of the singly oxygenated species were obtained with the Beaucage reagent (FIG. 5B) and DtsNH (FIG. 5C). Approximately 13. 1% of the singly oxygenated species (corresponding to approximately 96% sulfurization efficiency) were obtained using the Beaucage reagent and DtsNH, respectively.

Figure 6A:
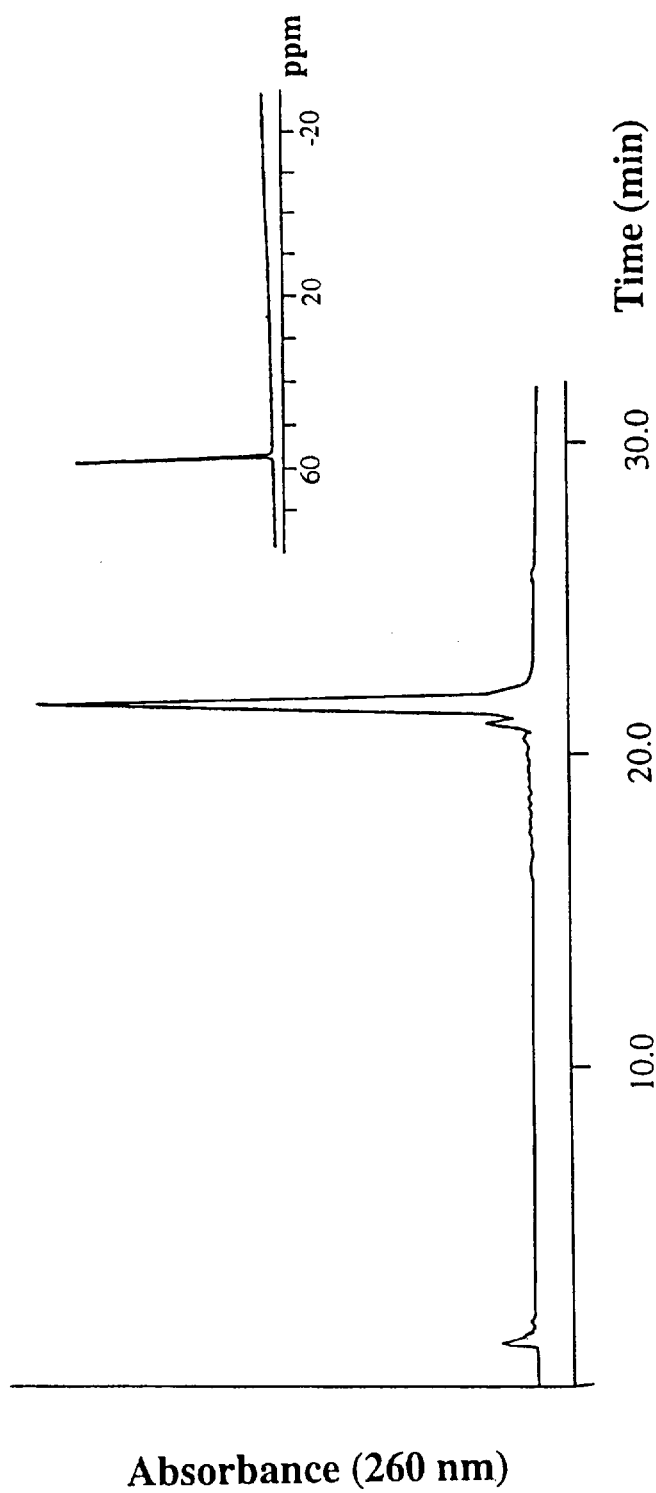
FIG. 6. Both anion-exchange HPLC and $^{31}$P NMR (insets) of the oligodeoxyribonucleotide S-$U_{19}$A containing multiple phosphorothioate linkages, established by 2 minute reaction time with 0.05M sulfurizing reagent in acetonitrile. (A) Sulfurization reaction was performed by EDITH; and (B) sulfurization reaction was performed by the Beaucage reagent.
Figure 6B:
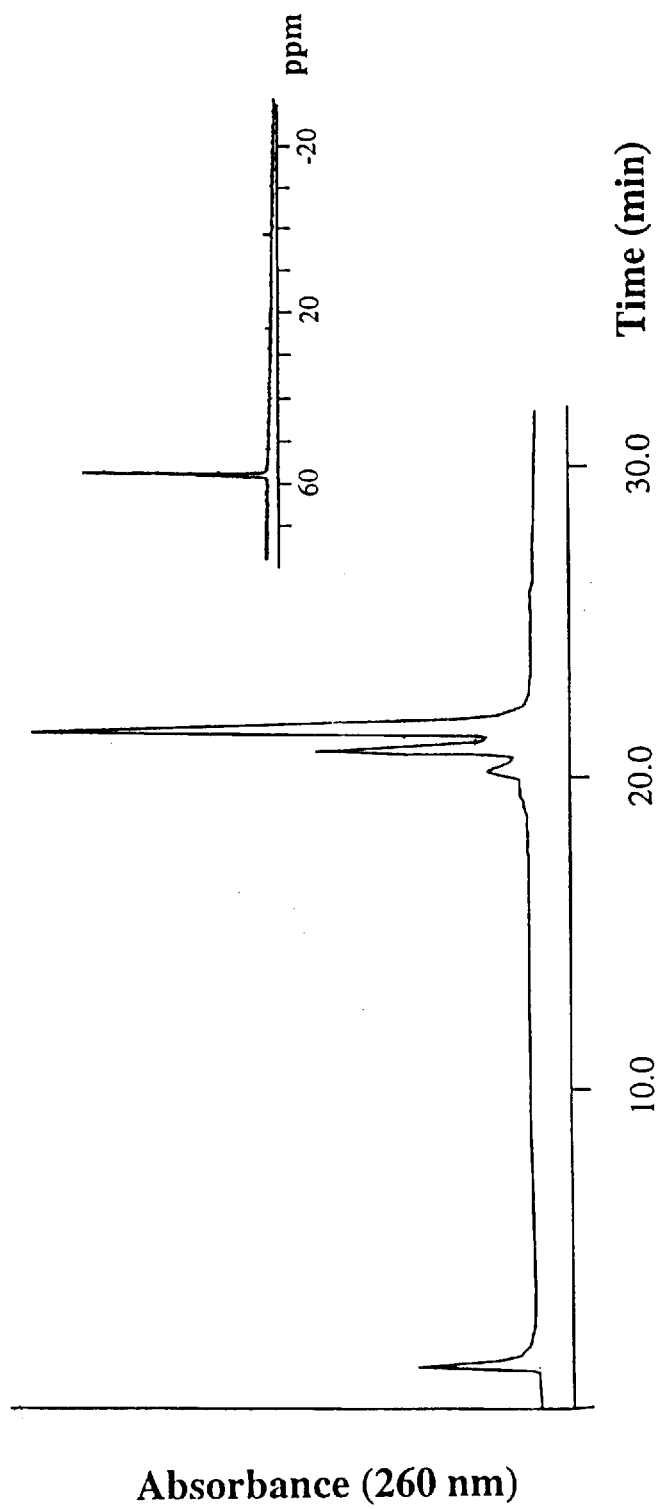

EDITH was just as effective in sulfurizing a longer 20-mer RNA oligonucleotide at multiple positions. A direct comparison of the anion exchange HPLC results obtained with the sequences S-$U_{19}$A prepared with either EDITH (FIG. 6A) or the Beaucage reagent (FIG. 6B) was carried out. Once again, the amount of singly oxygenated species (5.6%) indicates that greater than 99% sulfurization efficiency was obtained at each step using EDITH. The amount of singly oxygenated species obtained using the Beaucage reagent (27.5%) suggests that the sulfur transfer efficiency was only 98% at each step, very similar to the RNA hexamer result described above.

A mixed sequence 19-mer containing all 4 nucleobases was sulfurized using both EDITH and the Beaucage reagent and the results are presented in Table 3. The same sequence was prepared with a phosphorothioate at every position (sequence i) and at single positions (sequences ii and iii). In all cases, use of EDITH resulted in nearly quantitative sulfur transfer (Table 3, lines 7, 9, 10). The Beaucage reagent performed similarly to EDITH in the case of the singly-sulfurized sequence (Table 3, line 8). However, only 95% fully-sulfurized product was obtained using the Beaucage reagent in the synthesis of the multiply-sulfurized RNA 19-mer (Table 3, line 6).

EXAMPLE 8

Use of DtsNH for Thiophosphopeptide Synthesis Gly-Ser [P(S)$O_2 H_2$]-Phe-$NH_2$ Solid-phase synthesis was carried out starting with Fmoc-PAL-MBHA (0.19 mmol/g (Bioscience Division of PerSeptive Biosystems (Farmingham, Mass.) and adding $N^\alpha$-Fmoc-Phe-OH, $N^\alpha$-Fmoc-Ser-OH, and Boc-Gly-OH (Advanced ChemTech, Louisville, Ky.). Fmoc removal was with piperidine-DMF (1:4, 2+8 minutes) followed by washing with DMF (5×2 minutes) and $CH_2Cl_2$ (5×2 minutes). Couplings were achieved by combining solid protected amino acids (4.0 equivalents), 1-hydroxybenzotriazole (HOBt, PerSeptive Biosystems, Framingham, Mass., 4.0 equivalents), and benzotriazolyl N-oxytris-dimethylamino phosphonium hexafluorophospate (BOP, PerSeptive Biosystems, Farmingham, Mass., 4.0 equivalents), and N-methylmorpholine (NMM, Fisher, Pittsburgh, Pa., 8.0 equivalents) in DMF for 10 minutes under $N_2$ at 25° C., and then adding this pre-activated solution to the peptide resin. Single couplings were carried for 1 hour. Phosphorothiolation was carried out as follows: di-tert-butyl N,N-diethylphosphoramidite (10 equivalents) and 1H-tetrazole (50 equivalents) were dissolved under an argon atmosphere in dry tetrahydyrofuran (1.0 mL), and added to the resin with peptide containing the side-chain unprotected serine. The whole reaction was kept under argon atmosphere. After 1 hour at 25° C., the solvent was filtered and the resin was washed with THF (5×2 minutes) and $CH_2Cl_2$ (5×2 minutes). Then 0.045M DtsN$C_6H_5$ (prepared as described by Slomczynska and Barany, J. Heterocyclic Chem., 21, 241–246 (1984)) (1.2 equivalent) in $CH_2Cl_2$ was added to the resin, the reaction was kept under argon for 15 minutes. The solvent was filtered, and the resin was washed with DMF, $CH_2Cl_2$, and ether. Reagent R: TFA-thioanisole-1,2-ethanedithiol-anisole (90:5:3:2) was used for deprotection and cleavage fron the resin. The cleavage cocktail (5 mL) was prepared fresh, degassed with $N_2$ and added to the dry protected peptide-resin. After 3 hours at 25° C., the cleavage mixture was filtered, and washed with reagent R (2×2 mL). The peptide was precipitated fron the combined filtrates wtih diethyl ether (30 mL) at 0° C., collected by low-speed centrifugation, washed with cold ether (5×5 mL), dissolved in $H_2O$ (20 mL), and lyophilized. Analytical HPLC was performed using an analytical C-18 reversed-phase column, and a UV detector operating at 210 nm. The peptide samples were chromatographed at 1.0 mL/minute with 0.1% aqueous TFA—$CH_3CN$ (49:1 to 5:2 over 30 minutes). The product was characterized further by FAB-MS: expected, 404.1; obtained ($M^+$+H), 405.2.

EXAMPLE 9

Preparation of a dithiophosphonate-S-t-Butyl-O-Methyl-P-Methyl-Phosphonothioate

Under an inert atmosphere, a solution of dichlorotriphenylphosphorane (95% purity, Aldrich, 1.36 g, 3.9 mmol) in dry pyridine (15 mL) was added dropwise to a solution of S-t-Butyl-P-methyl-phosphonothioite (2.6 mmol, prepared according to Fernandez et al., *J. Org. Chem.*, 60, 7390–7391 (1995)), in dry pyridine (5 mL) to generate the chlorophosphonothioite which was then reacted in situ with dry methanol (2.6 mmol) for 30 minutes. The resulting phosphonothioite was reacted with DtsNH (0.7 g, 5.2 mmol) for 1 hour. Then the pyridine was evaporated and the residue was triturated with hexane (3×10 mL). The hexane phase was washed 3 times with saturated aqueous $NaHCO_3$ and dried with $Na_2SO_4$. The compound was purified by flash chromatography eluting with hexane-EtOAc (100:7). Yield: 50%. $^1$H NMR (250 MHz, $CDCl_3$) a 1.54 (s, 9H, t-Bu), 2.19 (d, $J_{PH}$=13.5 Hz, 3H, $CH_3$)), 3.72 (d, $J_{PH}$=15.3 Hz, 3H, $OCH_3$); $^{31}$P NMR (101 MHz, $CDCl_3$) δ98.8.MS (EI) m/e 198 (9), 142 (57), 109 (100), 77 (24), 57 (53) GC: $t_R$=7.8 minutes; purity: 80%; impurities: $CH_3P(S)(St-Bu)_2$, 13% [$^{31}$P NMR (101 MHz, $CDCl_3$) δ63.7.MS (El) m/e 256 (3), 200 (38), 144 (100), 111 (18), 110 (10), 79 (11), 57 (100); HRMS (EI) m/e calculated for $C_6H_{15}NOPS_2$: 198.0302; found: 198.0301. GC: $t_R$=10.5 minutes].

EXAMPLE 10

Preparation of Thiophosphonate and Thiophosphonamide Pseudodipeptides

According to the general procedure in Fernandez et al., *J. Org. Chem.*, 60, 7390–7391 (1995) (see Example 9), a solution of the phosphinate amino acid analogue, Boc-Val§P(O)(OtBu)H prepared according to Fernandez et al., *J. Org. Chem.*, 60, 7390–7391 (1995), (0.4 mmol) in $CH_2Cl_2$ (1 mL) was activated by addition of dichlorotriphenylphosphorane (0.21 g, 0.6 mmol) in dry pyridine (3 ml). After 30 minutes, this solution was then reacted with methyl (S) lactate (0.4 mmol) or glycine ethyl ester hydrochloride (0.4 mmol; free base formed in situ by addition of $Et_3N$, 1.4 mmol, to glycine ethyl ester solution prior to reaction with phosphonochloridite). Sulfurization was again accomplished by addition of solid DtsNH (108 mg., 0.8 mmol) to the reaction mixtures.

The thiophosphonate dipeptide, Boc-Val§[P(S)(OtBu)O](S)Ala-$OCH_3$, was worked up as in Example 9 and purified by flash chromatography using EtOAc-hexane (1:10) as the eluent yielding a mixture of diastereomeric productions. Yield: 49 mg (30%). $^1$H NMR (300 MHz, $CDCl_3$) δ0.97 (m, 6H, $CH(CH_3)_2$), 1.45 (s, 9H, $(CH_3)_3COCO$), approximately 1.50 (m, 3H, $CH(CH_3)$, obscured by neighboring singlets, 1.55 (s, 9H, OtBu), 2.45, 2.49 (2m, 1H, $CH(CH_3)_2$), 3.77, 3.81 (2s, 3H $COOCH_3$), 3.99, 4.05 (2m, 1H, CHP), 4.73 (d, 1H, NH), 5.06 (m, 1H, $OCH(CH_3)$); $^{31}$P NMR (121.57 MHz, $CDCl_3$)δ85.4, 85.9. HRMS (FAB (MNBA)) m/e calculated for $C_7H_{35}NO_6PS$ ((M+H)+): 412.1923; found: 412.1946.

The thiophosphonamide dipeptide, Boc-Val§[P(S)(OtBu)NH]Gly-$OCH_2CH_3$, was worked up as for Example 9 and purified by flash chromatography using EtOAc-hexane (1:5) as the eluent provided two diastereomeric products. Total yield: 56 mg (40%). Diast. 1: $^1$H NMR (250 MHz, $CDCl_3$) δ1.03 (dd, 6H, $CH(CH_3)_2$), 1.27 (t, 3H, $COOCH_2CH_3$, 1.42 (s, 9H, $COOC(CH_3)_3$), 1.56 (s, 9H $OC(CH_3)_3$), 2.16 (m, 1H, $CH(CH_3)_2$), 3.27 (m, 1H, $NH(CH_2)$), 3.63 (m, 1H, CH), 3.90 (m, 2H, $NH(CH_2)$), 4.18 (q, 2H, $COOCH_2CH_3$), 4.88 (d, 1H, BocNH); $^{31}$P NMR (101 MHz, $CDCl_3$) δ71.98, HRMS (FAB (MNBA)) m/e calculated for $C_{17}H_{36}N_2O_5PS$ ((M+H)

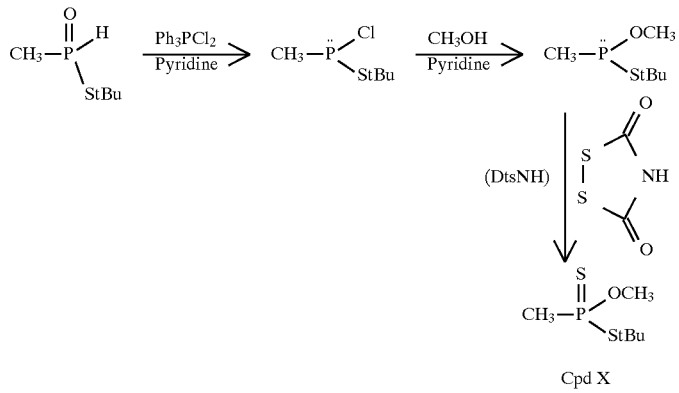

Cpd X

+): 411.2082; found: 411.2079. Diast 2: $^1$H NMR (250 MHz, $CDCl_3$) δ0.97 (dd, 6H, $CH(CH_3)_2$), 1.25 (t, 3H, $COOCH_2CH_3$), 1.46 (s, 9H, $COOC(CH_3)_3$), 1.52 (s, 9H, $OC(CH_3)_3$) 2.41 (m, 1H, $CH(CH_3)_2$), 3.35 (m, 1H, $NH(CH_2)$), 3.84 (m, 3H, CH, $NH(CH_2)$), 4.20, (q, 2H, $COOCH_2CH_3$), 4.83 (d, 1H, BocNH); $^{31}$p NMR (101 MHz, $CDCl_3$) δ70.97. HRMS (FAB (MNBA)) m/e calc'd for $Cl_7H_{36}N_2O_5PS$ ((M+H)+): 411.2082; found: 411.2096.

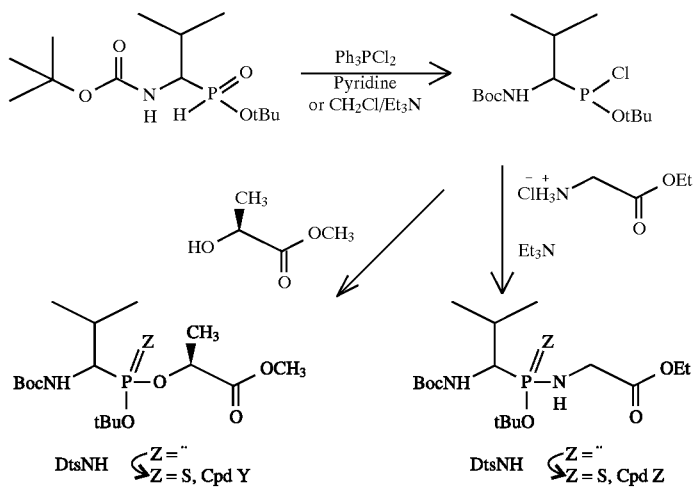

EXAMPLE 11

Solid-Phase Synthesis of Phosphorothioate DNA using EDITH on a Model 394 Applied Biosystems/Perkin Elmer Oligonucleotide Synthesizer An Applied Biosystems/Perkin Elmer (ABD/PE) Model 394 DNA Synthesizer was operated on either a 1.0 μmol scale, starting with controlled pore-glass (500 Å) supports loaded with the 3'-end deoxyC or deoxyA residue attached to the supports via a long chain alkylamino linker (dA-lcaa—CPG), and using P-cyanoethyl deoxyribonucleoside phosphoramidites and other standard solvents and reagents, all from ABD/PE (Foster City, Calif.). Sulfurization conditions and machine set-up were exactly as prescribed by ABD/PE for TETD except for the following changes: EDITH, 0.05M in $CH_3CN$ was used as the sulfurization reagent and the bottle placed in position 10 of the ABD/PE 394 (usually used for the ammonium hydroxide); the sulfurization cycle (replacing oxidation cycle at the specific position where phosphorothioate linkage desired) provided with Model 394 (for TETD) was modified to give two 30 second pulses or treatments (approximately 0.8 mL each pulse, total volume per cycle approximately 1.6 mL of EDITH solution) of the CPG-bound with the sulfurization reagent. The capping step in the synthesis cycle was performed after the sulfurization reaction, in order to avoid premature oxidation of the phosphite linkage. The remaining steps in the synthesis cycle were performed according to standard methods (ABD/PE). Upon completion of solid-phase steps, the oligodeoxyribonucleotides were released from the support and deblocked with 30% ammonium hydroxide (15 hours, 55° C.) and desalted on $C_{18}$ Sep-Pak cartridges (Millipore), lyophilized, and analyzed by C-1 8 reversed-phase and/or anion exchange HPLC and MALDI-TOF MS. The following sequences were made: 5'-$C_SC_SC_SC_SC$-3'; 5'-$C_SA_ST_SG_SC$-3'; and 5'-$A_SC_SC_SC_SC_SA_SG_SA_SA_SC_SA_ST_SC_SA_S$T-3'. All were greater than 95% pure by HPLC and gave the correct mass [(M–H)⁻] by MALDI-MS.

The complete disclosure of all patents, patent documents, and publications cited herein are incorporated by reference as if each were individually incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of sulfurizing a phosphorus-containing compound, comprising contacting the phosphorus-containing compound with a compound of the formula (Formula I):

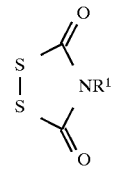

or a compound of the formula (Formula II):

wherein:
(a) $Y=R^2$, $OR^3$, $NR^{16}R^{17}$, or $SR^{18}$;
(b) each $R^1$, $R^{16}$, and $R^{17}$ is independently H or an organic group; and
(c) each $R^2$, $R^3$, and $R^{18}$ is independently an organic group.

2. The method of claim 1 wherein each $R^1$, $R^2$, $R^3$, $R^{16}$, $R^{17}$, and $R^{18}$ is independently an organic group having 1–carbon atoms.

3. The method of claim 2 wherein each $R^1$, $R^2$, $R^3$, $R^{16}$, $R^{17}$, and $R^{18}$ is independently an alkyl group or an aryl group.

4. The method of claim 3 wherein each $R^1$, $R^2$, $R^3$, $R^{16}$, $R^{17}$, and $R^{18}$ is independently a $(C_1-C_{10})$alkyl group.

5. The method of claim 4 wherein each $R^1$, $R^2$, $R^3$, $R^{16}$, $R^{17}$, and $R^{18}$ is independently a $(C_1-C_4)$alkyl group.

6. The method of claim 1 wherein the compound of Formula I is

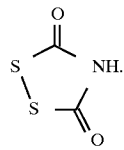

7. The method of claim 1 wherein the compound of Formula II is

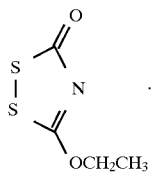

8. The method of claim 1 wherein the phosphorus-containing compound is a trivalent phosphorus compound.

9. The method of claim 8 wherein the trivalent phosphorus compound is of the formula (Formula III):

wherein X, W, and Z are organic groups.

10. The method of claim 9 wherein:
   (a) X and Z are independently selected from the group consisting of —R⁴, —O—R⁵, —C(R⁶)(R⁷)(R⁸), —NH(R⁹), —N(R¹⁰)(R¹¹) or —S—R¹²;
   (b) W is selected from the group consisting of —R⁴, —O—R⁵, —C(R⁶)(R⁷)(R⁸), —NH(R⁹), —N(R¹⁰)(R¹¹) or —S—R¹², halogen, or a protecting group; and
   (c) each R group is independently selected from the group consisting of aryl groups, alkyl groups, alicyclic groups, carbohydrate groups, glyceride groups, peptide groups, nucleoside groups, amino acid groups, steroidal groups, terpene groups, oligonucleotide groups, phosphonopeptide groups, phospholipid groups, phosphorus-containing polymeric groups, and phosphonate-modified surfaces.

11. The method of claim 10 wherein each R group is independently an alkyl group, peptide group, or oligonucleotide group.

12. The method of claim 11 wherein the oligonucleotide group comprises RNA or DNA.

13. The method of claim 1 wherein the step of contacting comprises combining the compounds in a solvent at a temperature within a range of about 0°–50° C.

14. The method of claim 13 wherein the sulfurization occurs in less than about 1 hour.

15. A method of sulfurizing a trivalent phosphorus compound of the formula (Formula III):

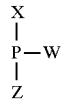

wherein X, W, and Z are organic groups, comprising contacting the compound of Formula III with a compound of the formula (Formula I):

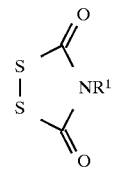

or a compound of the formula (Formula II):

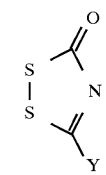

wherein:
   (a) Y=R², OR³, NR¹⁶R¹⁷, or SR¹⁸;
   (b) each R¹, R¹⁶, and R¹⁷ is independently H or an organic group having 1–carbon atoms; and
   (c) each R², R³, and R¹⁸ is independently an organic group having 1–carbon atoms.

16. The method of claim 15 wherein:
   (a) X and Z are independently selected from the group consisting of —R⁴, —O—R⁵, —C(R⁶)(R⁷)(R⁸), —NH(R⁹), —N(R¹⁰)(R¹¹) or —S—R¹²;
   (b) W is selected from the group consisting of —R⁴, —O—R⁵, —C(R⁶)(R⁷)(R⁸), —NH(R⁹), —N(R¹⁰)(R¹¹) or —S—R¹², halogen, or a protecting group; and
   (c) each R group is independently selected from the group consisting of aryl groups, alkyl groups, alicyclic groups, carbohydrate groups, glyceride groups, peptide groups, nucleoside groups, amino acid groups, steroidal groups, terpene groups, oligonucleotide groups, phosphonopeptide groups, phospholipid groups, phosphorus-containing polymeric groups, and phosphonate-modified surfaces.

17. The method of claim 15 wherein each R¹, R², R³, R¹⁶, R¹⁷, and R¹⁸ is independently an alkyl group or an aryl group.

18. The method of claim 17 wherein each R¹, R², R³, R¹⁶, R¹⁷, and R¹⁸ is independently a (C₁–C₁₀)alkyl group.

19. The method of claim 17 wherein each R¹, R², R³, R¹⁶, R¹⁷, and R¹⁸ is independently a (C₁–C₄)alkyl group.

20. The method of claim 15 wherein the compound of Formula I is

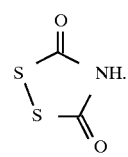

21. The method of claim 15 wherein the compound of Formula II is

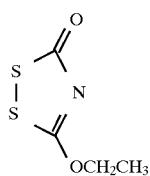

22. The method of claim 1 wherein the phosphorus-containing compound is selected from the group consisting of a nucleic acid, a phosphopeptide, a phosphorylated nucleoside sugar, and an oligosaccharide.

23. The method of claim 1 wherein the phosphorus-containing compound is a nucleic acid selected from the group consisting of DNA and RNA.

24. The method of claim 1 wherein the phosphorus-containing compound is a phosphopeptide selected from the group consisting of a phosphoropeptide and a phosphonopeptide.

25. The method of claim 1 performed during the synthesis of a phosphorus-containing compound selected from the group consisting of a nucleic acid, a phosphopeptide, a phosphorylated nucleoside sugar and an oligosaccharide.

26. The method of claim 25 wherein the synthesis of the phosphorus-containing compound is performed in the solid phase.

27. The method of claim 25 wherein the phosphorus-containing compound is a nucleic acid.

UNITED STATES PATENT AND TRADEMARK OFFICE
CERTIFICATE OF CORRECTION

PATENT NO.: 5,852,168
DATED: December 22, 1998
INVENTOR(S): Barany et al.

It is certified that error appears in the above-identified patent and that said Letters Patent is hereby corrected as shown below:

Face page, Assignee, after "State University," insert --and Agricultural and Mechanical College--;

Column 3, line 63, delete "1-carbon" and insert --1-20 carbon--;

Column 3, lines 64-65, delete "thioamide (thiourea, or dithiocarbamate, a thiocarbamate, dithiocarbamate, or thiourea)" and insert --thioamide, a thiocarbamate, thiourea, or dithiocarbamate--;

Column 4, line 13, delete "Tris-Hcl," and insert --Tris•HCl,--;

Column 5, line 23, delete "1-carbon" and insert --1-20 carbon--;

Column 7, line 66, delete "lycine" and insert --glycine--;

Column 13, line 4, delete "6 192.0" and insert --δ 192.0--;

Column 13, line 50, delete "[M$^+$-1)," and insert --(M-1)$^-$,--;

Column 13, line 52, delete "(M+," and insert --(M$^+$--;

Column 14, line 35, delete "(CDCl$_3$)" and insert --(CDCl$_3$)--;

Column 16, line 61, delete "31P" and insert --$^{31}$P--;

Column 20, TABLE 3, delete "P NMR" and insert --$^{31}$P NMR--;

UNITED STATES PATENT AND TRADEMARK OFFICE
CERTIFICATE OF CORRECTION

PATENT NO.: 5,852,168
DATED: December 22, 1998
INVENTOR(S): Barany et al.

It is certified that error appears in the above-identified patent and that said Letters Patent is hereby corrected as shown below:

Column 21, line 34, delete "a 1.54" and insert --δ 1.54--;

Column 22, line 7, delete "Boc-Val §P" and insert --Boc-ValψP--;

Column 22, line 19, delete "Boc-Val §" and insert --Boc-Valψ--;

Column 22, line 29, delete "$C_7H_{35}NO_6PS$" and insert --$C_{17}H_{35}NO_6PS$--;

Column 22, line 29, delete "((M+H)+):" and insert --$((M+H)^+)$:--;

Column 22, line 31, delete "Boc-Val§" and insert --Boc-Valψ--;

Column 22, line 60, delete "+):" and insert --$^+)$:--;

Column 22, line 66, delete "$^{31}$p" and insert --$^{31}P$--;

Column 23, line 1, delete "$Cl_7$" and insert --$C_{17}$--;

Column 23, line 1, delete "((M+H)+):" and insert --$((M+H)^+)$:--;

Column 23, line 33, delete "P-cyanoethyl" and inert --β-cyanoethyl--;

Column 23, line 45, after "cycle", insert -- = --;

Column 23, line 55, delete "C-1 8" and insert --C-18--;

UNITED STATES PATENT AND TRADEMARK OFFICE
CERTIFICATE OF CORRECTION

PATENT NO.: 5,852,168
DATED: December 22, 1998
INVENTOR(S): Barany et al.

It is certified that error appears in the above-identified patent and that said Letters Patent is hereby corrected as shown below:

Column 24, line 58, delete "1-carbon" and insert --1-20 carbon--;

Column 26, line 27, delete "1-carbon" and insert --1-20 carbon--;

Column 26, line 30, delete "1-carbon" and insert --1-20 carbon--; and

Column 28, line 12, delete "25" and insert --26--.

Signed and Sealed this

Eighth Day of May, 2001

*Attest:*

NICHOLAS P. GODICI

*Attesting Officer*    Acting Director of the United States Patent and Trademark Office